US009326864B2

(12) United States Patent
Wyss et al.

(10) Patent No.: US 9,326,864 B2
(45) Date of Patent: *May 3, 2016

(54) ORTHOPAEDIC KNEE PROSTHESIS HAVING CONTROLLED CONDYLAR CURVATURE

(71) Applicant: DePuy (Ireland), Cork (IE)

(72) Inventors: Joseph G. Wyss, Fort Wayne, IN (US);
Christel M. Wagner, Plymouth, IN (US); Dimitri Sokolov, Copley, OH (US); Jordan S. Lee, Warsaw, IN (US); John L. Williams, Fort Wayne, IN (US); Said T. Gomaa, Fort Wayne, IN (US); John M. Armacost, Warsaw, IN (US)

(73) Assignee: DePuy (Ireland) (IE)

( * ) Notice: Subject to any disclaimer, the term of this patent is extended or adjusted under 35 U.S.C. 154(b) by 0 days.

This patent is subject to a terminal disclaimer.

(21) Appl. No.: 14/486,085

(22) Filed: Sep. 15, 2014

(65) Prior Publication Data
US 2015/0005888 A1    Jan. 1, 2015

Related U.S. Application Data

(63) Continuation of application No. 13/481,943, filed on May 28, 2012, now Pat. No. 8,834,575, which is a continuation of application No. 12/165,575, filed on Jun. 30, 2008, now Pat. No. 8,187,335.

(51) Int. Cl.
*A61F 2/38* (2006.01)
*A61F 2/30* (2006.01)

(52) U.S. Cl.
CPC .............. *A61F 2/3886* (2013.01); *A61F 2/3859* (2013.01); *A61F 2/3868* (2013.01); *A61F 2002/30116* (2013.01); *A61F 2002/30332* (2013.01); *A61F 2220/0033* (2013.01); *A61F 2230/0006* (2013.01); *A61F 2310/00179* (2013.01)

(58) Field of Classification Search
None
See application file for complete search history.

(56) References Cited

U.S. PATENT DOCUMENTS 3,765,033 A    10/1973    Goldberg et al.
3,840,905 A    10/1974    Deane (Continued)

FOREIGN PATENT DOCUMENTS

CN    1803106 A    7/2006
CN    1872009 A    12/2006

(Continued)

OTHER PUBLICATIONS

European Search Report for European Patent Application No. 09164235.5-1526, Dec. 22, 2009, 6 pgs.

(Continued)

*Primary Examiner* — David H Willse
*Assistant Examiner* — Javier Blanco
(74) *Attorney, Agent, or Firm* — Barnes & Thornburg LLP

(57) ABSTRACT

An orthopaedic knee prosthesis includes a tibial bearing and a femoral component configured to articulate with the tibial bearing. The femoral component includes a posterior cam configured to contact a spine of the tibial bearing and a condyle surface curved in the sagittal plane. The radius of curvature of the condyle surface decreases gradually between early-flexion and mid-flexion. Additionally, in some embodiments, the radius of curvature of the condyle surface may be increased during mid-flexion.

16 Claims, 16 Drawing Sheets

(56) References Cited

U.S. PATENT DOCUMENTS

| | | |
|---|---|---|
| 3,852,045 A | 12/1974 | Wheeler et al. |
| 3,855,638 A | 12/1974 | Pilliar |
| 3,869,731 A | 3/1975 | Waugh et al. |
| 4,081,866 A | 4/1978 | Upshaw et al. |
| 4,156,943 A | 6/1979 | Collier |
| 4,206,516 A | 6/1980 | Pilliar |
| 4,209,861 A | 7/1980 | Walker et al. |
| 4,215,439 A | 8/1980 | Gold et al. |
| 4,249,270 A | 2/1981 | Bahler et al. |
| 4,257,129 A | 3/1981 | Volz |
| 4,262,368 A | 4/1981 | Lacey |
| 4,340,978 A | 7/1982 | Buechel et al. |
| 4,470,158 A | 9/1984 | Pappas et al. |
| 4,612,160 A | 9/1986 | Donlevy et al. |
| 4,673,407 A | 6/1987 | Martin |
| 4,714,474 A | 12/1987 | Brooks, Jr. et al. |
| 4,795,468 A | 1/1989 | Hodorek et al. |
| 4,808,185 A | 2/1989 | Penenberg et al. |
| 4,822,362 A | 4/1989 | Walker et al. |
| 4,838,891 A | 6/1989 | Branemark et al. |
| 4,888,021 A | 12/1989 | Forte et al. |
| 4,938,769 A | 7/1990 | Shaw |
| 4,944,757 A | 7/1990 | Martinez et al. |
| 4,944,760 A | 7/1990 | Kenna |
| 4,950,298 A | 8/1990 | Gustilo et al. |
| 4,963,152 A | 10/1990 | Hofmann et al. |
| 4,990,163 A | 2/1991 | Ducheyne et al. |
| 5,007,933 A | 4/1991 | Sidebotham et al. |
| 5,011,496 A | 4/1991 | Forte et al. |
| 5,019,103 A | 5/1991 | Van Zile et al. |
| 5,037,423 A | 8/1991 | Kenna |
| 5,071,438 A | 12/1991 | Jones et al. |
| 5,080,675 A | 1/1992 | Lawes et al. |
| 5,104,410 A | 4/1992 | Chowdhary |
| 5,108,442 A | 4/1992 | Smith |
| 5,116,375 A | 5/1992 | Hofmann |
| 5,133,758 A | 7/1992 | Hollister |
| 5,147,405 A | 9/1992 | Van Zile et al. |
| 5,171,283 A | 12/1992 | Pappas et al. |
| 5,201,766 A | 4/1993 | Georgette |
| 5,219,362 A | 6/1993 | Tuke et al. |
| 5,236,461 A | 8/1993 | Forte |
| 5,251,468 A | 10/1993 | Lin et al. |
| 5,258,044 A | 11/1993 | Lee |
| 5,271,737 A | 12/1993 | Baldwin et al. |
| 5,282,861 A | 2/1994 | Kaplan |
| 5,308,556 A | 5/1994 | Bagley |
| 5,309,639 A | 5/1994 | Lee |
| 5,326,361 A | 7/1994 | Hollister |
| 5,330,533 A | 7/1994 | Walker |
| 5,330,534 A | 7/1994 | Herrington et al. |
| 5,344,460 A | 9/1994 | Turanyi et al. |
| 5,344,461 A | 9/1994 | Philpot |
| 5,344,494 A | 9/1994 | Davidson et al. |
| 5,358,527 A | 10/1994 | Forte |
| 5,368,881 A | 11/1994 | Kelman et al. |
| 5,370,699 A | 12/1994 | Hood et al. |
| 5,387,240 A | 2/1995 | Pottenger et al. |
| 5,395,401 A | 3/1995 | Bahler |
| 5,405,396 A | 4/1995 | Heldreth et al. |
| 5,413,604 A | 5/1995 | Hodge |
| 5,414,049 A | 5/1995 | Sun et al. |
| 5,449,745 A | 9/1995 | Sun et al. |
| 5,458,637 A | 10/1995 | Hayes |
| 5,480,446 A | 1/1996 | Goodfellow et al. |
| 5,543,471 A | 8/1996 | Sun et al. |
| 5,549,686 A | 8/1996 | Johnson et al. |
| 5,571,187 A | 11/1996 | Devanathan |
| 5,571,194 A | 11/1996 | Gabriel |
| 5,609,639 A | 3/1997 | Walker |
| 5,609,643 A | 3/1997 | Colleran et al. |
| 5,639,279 A | 6/1997 | Burkinshaw et al. |
| 5,650,485 A | 7/1997 | Sun et al. |
| 5,658,333 A | 8/1997 | Kelman et al. |
| 5,658,342 A | 8/1997 | Draganich et al. |
| 5,658,344 A | 8/1997 | Hurlburt |
| 5,681,354 A | 10/1997 | Eckhoff |
| 5,683,468 A | 11/1997 | Pappas |
| 5,702,458 A | 12/1997 | Burstein et al. |
| 5,702,463 A | 12/1997 | Pothier et al. |
| 5,702,464 A | 12/1997 | Lackey et al. |
| 5,702,466 A | 12/1997 | Pappas et al. |
| 5,725,584 A | 3/1998 | Walker et al. |
| 5,728,748 A | 3/1998 | Sun et al. |
| 5,732,469 A | 3/1998 | Hamamoto et al. |
| 5,755,800 A | 5/1998 | O'Neil et al. |
| 5,755,801 A | 5/1998 | Walker et al. |
| 5,755,803 A | 5/1998 | Haines et al. |
| 5,765,095 A | 6/1998 | Flak et al. |
| 5,766,257 A | 6/1998 | Goodman et al. |
| 5,776,201 A | 7/1998 | Colleran et al. |
| 5,800,552 A | 9/1998 | Forte |
| 5,811,543 A | 9/1998 | Hao et al. |
| 5,824,096 A | 10/1998 | Pappas et al. |
| 5,824,100 A | 10/1998 | Kester et al. |
| 5,824,102 A | 10/1998 | Buscayret |
| 5,824,103 A | 10/1998 | Williams |
| 5,871,543 A | 2/1999 | Hofmann |
| 5,871,545 A | 2/1999 | Goodfellow et al. |
| 5,871,546 A | 2/1999 | Colleran et al. |
| 5,879,394 A | 3/1999 | Ashby et al. |
| 5,879,400 A | 3/1999 | Merrill et al. |
| 5,906,644 A | 5/1999 | Powell |
| 5,935,173 A | 8/1999 | Roger et al. |
| 5,951,603 A | 9/1999 | O'Neil et al. |
| 5,957,979 A | 9/1999 | Beckman et al. |
| 5,964,808 A | 10/1999 | Blaha et al. |
| 5,976,147 A | 11/1999 | LaSalle et al. |
| 5,984,969 A | 11/1999 | Matthews et al. |
| 5,989,027 A | 11/1999 | Wagner et al. |
| 5,997,577 A | 12/1999 | Herrington et al. |
| 6,004,351 A | 12/1999 | Tomita et al. |
| 6,005,018 A | 12/1999 | Cicierega et al. |
| 6,010,534 A | 1/2000 | O'Neil et al. |
| 6,013,103 A | 1/2000 | Kaufman et al. |
| 6,017,975 A | 1/2000 | Saum et al. |
| 6,039,764 A | 3/2000 | Pottenger et al. |
| 6,042,780 A | 3/2000 | Huang |
| 6,053,945 A | 4/2000 | O'Neil et al. |
| 6,059,949 A | 5/2000 | Gal-Or et al. |
| 6,068,658 A | 5/2000 | Insall et al. |
| 6,080,195 A | 6/2000 | Colleran et al. |
| 6,090,144 A | 7/2000 | Letot et al. |
| 6,123,728 A | 9/2000 | Brosnahan et al. |
| 6,123,729 A | 9/2000 | Insall et al. |
| 6,123,896 A | 9/2000 | Meeks, III et al. |
| 6,126,692 A | 10/2000 | Robie et al. |
| 6,135,857 A | 10/2000 | Shaw et al. |
| 6,139,581 A | 10/2000 | Engh et al. |
| 6,152,960 A | 11/2000 | Pappas |
| 6,162,254 A | 12/2000 | Timoteo |
| 6,174,934 B1 | 1/2001 | Sun et al. |
| 6,206,926 B1 | 3/2001 | Pappas |
| 6,210,444 B1 | 4/2001 | Webster et al. |
| 6,210,445 B1 | 4/2001 | Zawadzki |
| 6,217,618 B1 | 4/2001 | Hileman |
| 6,228,900 B1 | 5/2001 | Shen et al. |
| 6,238,434 B1 | 5/2001 | Pappas |
| 6,242,507 B1 | 6/2001 | Saum et al. |
| 6,245,276 B1 | 6/2001 | McNulty et al. |
| 6,258,127 B1 | 7/2001 | Schmotzer |
| 6,264,697 B1 | 7/2001 | Walker |
| 6,280,476 B1 | 8/2001 | Metzger et al. |
| 6,281,264 B1 | 8/2001 | Salovey et al. |
| 6,299,646 B1 | 10/2001 | Chambat et al. |
| 6,316,158 B1 | 11/2001 | Saum et al. |
| 6,319,283 B1 | 11/2001 | Insall et al. |
| 6,325,828 B1 | 12/2001 | Dennis et al. |
| 6,344,059 B1 | 2/2002 | Krakovits et al. |
| 6,361,564 B1 | 3/2002 | Marceaux et al. |
| 6,372,814 B1 | 4/2002 | Sun et al. |
| 6,379,388 B1 | 4/2002 | Ensign et al. |
| 6,428,577 B1 | 8/2002 | Evans et al. |
| 6,443,991 B1 | 9/2002 | Running |

(56) References Cited

U.S. PATENT DOCUMENTS

| | | |
|---|---|---|
| 6,475,241 B2 | 11/2002 | Pappas |
| 6,485,519 B2 | 11/2002 | Meyers et al. |
| 6,491,726 B2 | 12/2002 | Pappas |
| 6,494,914 B2 | 12/2002 | Brown et al. |
| 6,503,280 B2 | 1/2003 | Repicci |
| 6,506,215 B1 | 1/2003 | Letot et al. |
| 6,506,216 B1 | 1/2003 | McCue et al. |
| 6,524,522 B2 | 2/2003 | Vaidyanathan et al. |
| 6,540,787 B2 | 4/2003 | Biegun et al. |
| 6,558,426 B1 | 5/2003 | Masini |
| 6,569,202 B2 | 5/2003 | Whiteside |
| 6,582,469 B1 | 6/2003 | Tornier |
| 6,582,470 B1 | 6/2003 | Lee et al. |
| 6,589,283 B1 | 7/2003 | Metzger et al. |
| 6,592,787 B2 | 7/2003 | Pickrell et al. |
| 6,620,198 B2 | 9/2003 | Burstein et al. |
| 6,623,526 B1 | 9/2003 | Lloyd |
| 6,645,251 B2 | 11/2003 | Salehi et al. |
| 6,660,039 B1 | 12/2003 | Evans et al. |
| 6,660,224 B2 | 12/2003 | Lefebvre et al. |
| 6,664,308 B2 | 12/2003 | Sun et al. |
| 6,702,821 B2 | 3/2004 | Bonutti |
| 6,719,800 B2 | 4/2004 | Meyers et al. |
| 6,726,724 B2 | 4/2004 | Repicci |
| 6,730,128 B2 | 5/2004 | Burstein |
| 6,764,516 B2 | 7/2004 | Pappas |
| 6,770,078 B2 | 8/2004 | Bonutti |
| 6,770,099 B2 | 8/2004 | Andriacchi et al. |
| 6,773,461 B2 | 8/2004 | Meyers et al. |
| 6,797,005 B2 | 9/2004 | Pappas |
| 6,818,020 B2 | 11/2004 | Sun et al. |
| 6,846,327 B2 | 1/2005 | Khandkar et al. |
| 6,846,329 B2 | 1/2005 | McMinn |
| 6,849,230 B1 | 2/2005 | Feichtinger |
| 6,852,272 B2 | 2/2005 | Artz et al. |
| 6,869,448 B2 | 3/2005 | Tuke et al. |
| 6,893,388 B2 | 5/2005 | Reising et al. |
| 6,893,467 B1 | 5/2005 | Bercovy |
| 6,916,340 B2 | 7/2005 | Metzger et al. |
| 6,923,832 B1 | 8/2005 | Sharkey et al. |
| 6,926,738 B2 | 8/2005 | Wyss |
| 6,942,670 B2 | 9/2005 | Heldreth et al. |
| 6,972,039 B2 | 12/2005 | Metzger et al. |
| 6,986,791 B1 | 1/2006 | Metzger |
| 7,025,788 B2 | 4/2006 | Metzger et al. |
| 7,048,741 B2 | 5/2006 | Swanson |
| 7,066,963 B2 | 6/2006 | Naegerl |
| 7,070,622 B1 | 7/2006 | Brown et al. |
| 7,081,137 B1 | 7/2006 | Servidio |
| 7,094,259 B2 | 8/2006 | Tarabichi |
| 7,101,401 B2 | 9/2006 | Brack |
| 7,104,996 B2 | 9/2006 | Bonutti |
| 7,105,027 B2 | 9/2006 | Lipman et al. |
| 7,147,819 B2 | 12/2006 | Bram et al. |
| 7,160,330 B2 | 1/2007 | Axelson, Jr. et al. |
| 7,175,665 B2 | 2/2007 | German et al. |
| 7,255,715 B2 | 8/2007 | Metzger |
| 7,261,740 B2 | 8/2007 | Tuttle et al. |
| 7,297,164 B2 | 11/2007 | Johnson et al. |
| 7,326,252 B2 | 2/2008 | Otto et al. |
| 7,341,602 B2 | 3/2008 | Fell et al. |
| 7,344,460 B2 | 3/2008 | Gait |
| 7,357,817 B2 | 4/2008 | D'Alessio, II |
| 7,422,605 B2 | 9/2008 | Burstein et al. |
| 7,510,557 B1 | 3/2009 | Bonutti |
| 7,527,650 B2 | 5/2009 | Johnson et al. |
| 7,572,292 B2 | 8/2009 | Crabtree et al. |
| 7,578,850 B2 | 8/2009 | Kuczynski et al. |
| 7,608,079 B1 | 10/2009 | Blackwell et al. |
| 7,611,519 B2 | 11/2009 | Lefevre et al. |
| 7,615,054 B1 | 11/2009 | Bonutti |
| 7,618,462 B2 | 11/2009 | Ek |
| 7,628,818 B2 | 12/2009 | Hazebrouck et al. |
| 7,635,390 B1 | 12/2009 | Bonutti |
| 7,658,767 B2 | 2/2010 | Wyss |
| 7,678,151 B2 | 3/2010 | Ek |
| 7,678,152 B2 | 3/2010 | Suguro et al. |
| 7,708,740 B1 | 5/2010 | Bonutti |
| 7,708,741 B1 | 5/2010 | Bonutti |
| 7,740,662 B2 | 6/2010 | Barnett et al. |
| 7,749,229 B1 | 7/2010 | Bonutti |
| 7,753,960 B2 | 7/2010 | Cipolletti et al. |
| 7,771,484 B2 | 8/2010 | Campbell |
| 7,776,044 B2 | 8/2010 | Pendleton et al. |
| 7,806,896 B1 | 10/2010 | Bonutti |
| 7,806,897 B1 | 10/2010 | Bonutti |
| 7,837,736 B2 | 11/2010 | Bonutti |
| 7,842,093 B2 | 11/2010 | Peters et al. |
| 7,875,081 B2 | 1/2011 | Lipman et al. |
| 7,922,771 B2 | 4/2011 | Otto et al. |
| 8,187,335 B2 | 5/2012 | Wyss et al. |
| 8,192,498 B2 | 6/2012 | Wagner et al. |
| 8,206,451 B2 | 6/2012 | Wyss et al. |
| 8,236,061 B2 | 8/2012 | Heldreth et al. |
| 8,734,522 B2 | 5/2014 | Wyss et al. |
| 8,784,496 B2 | 7/2014 | Wagner et al. |
| 8,795,380 B2 | 8/2014 | Heldreth et al. |
| 8,828,086 B2 | 9/2014 | Williams et al. |
| 8,834,575 B2 | 9/2014 | Wyss et al. |
| 2002/0138150 A1 | 9/2002 | Leclercq |
| 2003/0009232 A1 | 1/2003 | Metzger et al. |
| 2003/0035747 A1 | 2/2003 | Anderson et al. |
| 2003/0044301 A1 | 3/2003 | Lefebvre et al. |
| 2003/0075013 A1 | 4/2003 | Grohowski |
| 2003/0139817 A1 | 7/2003 | Tuke et al. |
| 2003/0153981 A1 | 8/2003 | Wang et al. |
| 2003/0171820 A1 | 9/2003 | Wilshaw et al. |
| 2003/0199985 A1 | 10/2003 | Masini |
| 2003/0212161 A1 | 11/2003 | McKellop et al. |
| 2003/0225456 A1 | 12/2003 | Ek |
| 2004/0015770 A1 | 1/2004 | Kimoto |
| 2004/0039450 A1 | 2/2004 | Griner et al. |
| 2004/0167633 A1 | 8/2004 | Wen et al. |
| 2004/0186583 A1 | 9/2004 | Keller |
| 2004/0215345 A1 | 10/2004 | Perrone, Jr. et al. |
| 2004/0243244 A1 | 12/2004 | Otto et al. |
| 2004/0243245 A1 | 12/2004 | Plumet et al. |
| 2005/0021147 A1 | 1/2005 | Tarabichi |
| 2005/0055102 A1 | 3/2005 | Tornier et al. |
| 2005/0059750 A1 | 3/2005 | Sun et al. |
| 2005/0069629 A1 | 3/2005 | Becker et al. |
| 2005/0096747 A1 | 5/2005 | Tuttle et al. |
| 2005/0100578 A1 | 5/2005 | Schmid et al. |
| 2005/0123672 A1 | 6/2005 | Justin et al. |
| 2005/0143832 A1 | 6/2005 | Carson |
| 2005/0154472 A1 | 7/2005 | Afriat |
| 2005/0203631 A1 | 9/2005 | Daniels et al. |
| 2005/0209701 A1 | 9/2005 | Suguro et al. |
| 2005/0209702 A1 | 9/2005 | Todd et al. |
| 2005/0249625 A1 | 11/2005 | Bram et al. |
| 2005/0278035 A1 | 12/2005 | Wyss et al. |
| 2006/0002810 A1 | 1/2006 | Grohowski, Jr. |
| 2006/0015185 A1 | 1/2006 | Chambat et al. |
| 2006/0036329 A1 | 2/2006 | Webster et al. |
| 2006/0052875 A1 | 3/2006 | Bernero et al. |
| 2006/0100714 A1 | 5/2006 | Ensign |
| 2006/0178749 A1 | 8/2006 | Pendleton et al. |
| 2006/0195195 A1 | 8/2006 | Burstein et al. |
| 2006/0228247 A1 | 10/2006 | Grohowski |
| 2006/0231402 A1 | 10/2006 | Clasen et al. |
| 2006/0241781 A1 | 10/2006 | Brown et al. |
| 2006/0257358 A1 | 11/2006 | Wen et al. |
| 2006/0271191 A1 | 11/2006 | Hermansson |
| 2006/0289388 A1 | 12/2006 | Yang et al. |
| 2007/0061014 A1 | 3/2007 | Naegerl |
| 2007/0073409 A1 | 3/2007 | Cooney, III et al. |
| 2007/0078521 A1 | 4/2007 | Overholser et al. |
| 2007/0100463 A1 | 5/2007 | Aram et al. |
| 2007/0129809 A1 | 6/2007 | Meridew et al. |
| 2007/0135926 A1 | 6/2007 | Walker |
| 2007/0173948 A1 | 7/2007 | Meridew et al. |
| 2007/0196230 A1 | 8/2007 | Hamman et al. |
| 2007/0203582 A1 | 8/2007 | Campbell |
| 2007/0219639 A1 | 9/2007 | Otto et al. |

(56) References Cited

U.S. PATENT DOCUMENTS

| | | |
|---|---|---|
| 2007/0293647 A1 | 12/2007 | McKellop et al. |
| 2008/0004708 A1 | 1/2008 | Wyss |
| 2008/0021566 A1 | 1/2008 | Peters et al. |
| 2008/0091272 A1 | 4/2008 | Aram et al. |
| 2008/0097616 A1 | 4/2008 | Meyers et al. |
| 2008/0114462 A1 | 5/2008 | Guidera et al. |
| 2008/0114464 A1 | 5/2008 | Barnett et al. |
| 2008/0119940 A1 | 5/2008 | Otto et al. |
| 2008/0161927 A1 | 7/2008 | Salvage et al. |
| 2008/0195108 A1 | 8/2008 | Bhatnagar et al. |
| 2008/0199720 A1 | 8/2008 | Liu |
| 2008/0206297 A1 | 8/2008 | Roeder et al. |
| 2008/0269596 A1 | 10/2008 | Revie et al. |
| 2009/0043396 A1 | 2/2009 | Komistek |
| 2009/0048680 A1 | 2/2009 | Naegerl |
| 2009/0082873 A1 | 3/2009 | Hazebrouck et al. |
| 2009/0084491 A1 | 4/2009 | Uthgenannt et al. |
| 2009/0088859 A1 | 4/2009 | Hazebrouck et al. |
| 2009/0125114 A1 | 5/2009 | May et al. |
| 2009/0192610 A1 | 7/2009 | Case et al. |
| 2009/0265012 A1 | 10/2009 | Engh et al. |
| 2009/0265013 A1 | 10/2009 | Mandell |
| 2009/0292365 A1 | 11/2009 | Smith et al. |
| 2009/0295035 A1 | 12/2009 | Evans |
| 2009/0306785 A1 | 12/2009 | Farrar et al. |
| 2009/0319047 A1 | 12/2009 | Walker |
| 2009/0326663 A1 | 12/2009 | Dun |
| 2009/0326664 A1 | 12/2009 | Wagner et al. |
| 2009/0326665 A1 | 12/2009 | Wyss et al. |
| 2009/0326666 A1 | 12/2009 | Wyss et al. |
| 2009/0326667 A1 | 12/2009 | Williams et al. |
| 2009/0326674 A1 | 12/2009 | Liu et al. |
| 2010/0016979 A1 | 1/2010 | Wyss et al. |
| 2010/0036499 A1 | 2/2010 | Pinskerova |
| 2010/0036500 A1 | 2/2010 | Heldreth et al. |
| 2010/0042224 A1 | 2/2010 | Otto et al. |
| 2010/0042225 A1 | 2/2010 | Shur |
| 2010/0063594 A1 | 3/2010 | Hazebrouck et al. |
| 2010/0070045 A1 | 3/2010 | Ek |
| 2010/0076563 A1 | 3/2010 | Otto et al. |
| 2010/0076564 A1 | 3/2010 | Schilling et al. |
| 2010/0094429 A1 | 4/2010 | Otto |
| 2010/0098574 A1 | 4/2010 | Liu et al. |
| 2010/0100189 A1 | 4/2010 | Metzger |
| 2010/0100190 A1 | 4/2010 | May et al. |
| 2010/0100191 A1 | 4/2010 | May et al. |
| 2010/0125337 A1 | 5/2010 | Grecco et al. |
| 2010/0161067 A1 | 6/2010 | Saleh et al. |
| 2010/0191341 A1 | 7/2010 | Byrd |
| 2010/0222890 A1 | 9/2010 | Barnett et al. |
| 2010/0286788 A1 | 11/2010 | Komistek |
| 2010/0292804 A1 | 11/2010 | Samuelson |
| 2010/0305710 A1 | 12/2010 | Metzger et al. |
| 2010/0312350 A1 | 12/2010 | Bonutti |
| 2011/0029090 A1 | 2/2011 | Zannis et al. |
| 2011/0029092 A1 | 2/2011 | Deruntz et al. |
| 2011/0035017 A1 | 2/2011 | Deffenbaugh et al. |
| 2011/0035018 A1 | 2/2011 | Deffenbaugh et al. |
| 2011/0106268 A1 | 5/2011 | Deffenbaugh et al. |
| 2011/0118847 A1 | 5/2011 | Lipman et al. |
| 2011/0125280 A1 | 5/2011 | Otto et al. |
| 2011/0153026 A1 | 6/2011 | Heggendorn et al. |
| 2012/0239158 A1 | 9/2012 | Wagner et al. |
| 2012/0259417 A1 | 10/2012 | Wyss et al. |
| 2012/0271428 A1 | 10/2012 | Heldreth et al. |
| 2012/0296437 A1 | 11/2012 | Wyss et al. |
| 2013/0006372 A1 | 1/2013 | Wyss et al. |
| 2013/0006373 A1 | 1/2013 | Wyss et al. |
| 2014/0228965 A1 | 8/2014 | Wyss et al. |
| 2014/0303740 A1 | 10/2014 | Heldreth et al. |
| 2014/0350686 A1 | 11/2014 | Williams et al. |
| 2015/0005888 A1 | 1/2015 | Wyss et al. |

FOREIGN PATENT DOCUMENTS

| | | |
|---|---|---|
| DE | 4308563 A1 | 9/1994 |
| DE | 19529824 A1 | 2/1997 |
| EP | 510178 | 5/1992 |
| EP | 0495340 A1 | 7/1992 |
| EP | 0634155 | 1/1995 |
| EP | 0636352 A2 | 2/1995 |
| EP | 0732091 A2 | 9/1996 |
| EP | 883388 | 12/1998 |
| EP | 0634156 B1 | 5/1999 |
| EP | 1129676 A1 | 5/2001 |
| EP | 0765645 B1 | 8/2003 |
| EP | 1374805 A2 | 2/2004 |
| EP | 1421918 A1 | 5/2004 |
| EP | 1440675 A1 | 7/2004 |
| EP | 1196118 | 10/2004 |
| EP | 1470801 | 10/2004 |
| EP | 0732092 B1 | 2/2005 |
| EP | 1591082 A2 | 2/2005 |
| EP | 1518521 A2 | 3/2005 |
| EP | 1226799 B1 | 5/2005 |
| EP | 1779812 A1 | 5/2007 |
| EP | 1923079 A1 | 5/2008 |
| EP | 2649965 | 10/2013 |
| FR | 2417971 A1 | 2/1979 |
| FR | 2621243 A1 | 4/1989 |
| FR | 2653992 A1 | 5/1991 |
| FR | 2780636 A1 | 1/2000 |
| FR | 2787012 A1 | 6/2000 |
| FR | 2809302 A1 | 11/2001 |
| FR | 2835178 A1 | 8/2003 |
| GB | 1065354 | 4/1967 |
| GB | 2293109 A | 3/1996 |
| GB | 2335145 A | 9/1999 |
| JP | 62205201 A | 9/1987 |
| JP | 8500992 T | 2/1996 |
| JP | H08-503407 A | 4/1996 |
| JP | 08224263 A | 9/1996 |
| JP | 2002291779 A | 10/2002 |
| JP | 2004167255 A | 6/2004 |
| JP | 2006015133 A | 1/2006 |
| WO | 7900739 | 10/1979 |
| WO | 8906947 | 8/1989 |
| WO | 9014806 | 12/1990 |
| WO | 9601725 | 1/1996 |
| WO | 9623458 | 8/1996 |
| WO | 9624311 | 8/1996 |
| WO | 9624312 | 8/1996 |
| WO | 9846171 | 10/1998 |
| WO | 9927872 | 6/1999 |
| WO | 9966864 | 12/1999 |
| WO | 0209624 A1 | 2/2002 |
| WO | 03039609 A1 | 5/2003 |
| WO | 03101647 A2 | 12/2003 |
| WO | 2004058108 A1 | 7/2004 |
| WO | 2004069104 A1 | 8/2004 |
| WO | 2005009489 A2 | 2/2005 |
| WO | 2005009729 A2 | 2/2005 |
| WO | 2005072657 A1 | 8/2005 |
| WO | 2005087125 A2 | 9/2005 |
| WO | 2006014294 A1 | 2/2006 |
| WO | 2006130350 A2 | 12/2006 |
| WO | 2007106172 A1 | 9/2007 |
| WO | 2007108804 A1 | 9/2007 |
| WO | 2007119173 A2 | 10/2007 |
| WO | 2008100784 A2 | 8/2008 |
| WO | 2009046212 A2 | 4/2009 |
| WO | 2009128943 A2 | 10/2009 |

OTHER PUBLICATIONS

European Search Report for European Patent Application No. 09164168.8-1526, Jan. 4, 2010, 6 pgs.

Vanguard Complete Knee System, Biomet, available at: http://www.biomet.com/patients/vanguard.sub.--complete.cfm, downloaded on Feb. 2009, (3 pages).

(56) References Cited

OTHER PUBLICATIONS

"NexGen Complete Knee Solution Cruciate Retaining Knee (CR)," Zimmer, available at: http://zimmer.com.au/ctl?template=PC&op=global&action=&template=PC&id=356- , downloaded on Feb. 18, 2009, (1 page).
Scorpio Knee TS Single Axis Revision Knee System, Stryker Orthopaedics, http://www.stryker.com/stellent/groups/public/documents/web.sub.--prod/02-3609.pdf, (6 pages).
P. Johal et al, "Tibio-femoral movement in the living knee. A study of weight bearing and non-weight bearing knee kinematics using 'interventional' MRI," Journal of Biomechanics, vol. 38, Issue 2, Feb. 2005, pp. 269-276, (8 pages).
Andriacchi, T.P., "The Effect of Knee Kinematics, Gait and Wear on the Short and Long-Term Outcomes of Primary Knee Replacement," NIH Consensus Development Conference on Total Knee Replacement, pp. 61-62, Dec. 8-10, 2003, (4 pages).
Asano et al. "In Vivo Three-Dimensional Knee Kinematics Using a Biplanar Image-Matching Technique," Clin Orthop Rel Res, 388: 157-166, 2001, (10 pages).
European Search Report for European Patent Application No. 09164160.5-1526, Jan. 4, 2010, 4 pgs.
European Search Report for European Patent Application No. 09164228.0-1526, Feb. 2, 2010, 6 pgs.
Kessler et al., "Sagittal curvature of total knee replacements predicts in vivo kinematics," Clinical Biomechanics 22(1): 52-58, 2007.
Wang et al., "Biomechanical differences exhibited during sit-to-stand between total knee arthroplasty designs of varying radii," J Arthroplasty 21(8): 1196-9, 2006.
Saari et al., "The effect of tibial insert design on rising from a chair; motion analysis after total knee replacement," Clin Biomech 19(9): 951-6, 2004.
Ranawat, "Design may be counterproductive for optimizing flexion after TKR," Clin Orthop Rel Res 416: 174-6, 2003.
D'Lima et al., "Quadriceps moment arm and quadriceps forces after total knee arthroplasty," Clin Orthop Rel Res 393:213-20, 2001.
Uvehammer et al., "In vivo kinematics of total knee arthroplasty: flat compared with concave tibial joint surface," J Orthop Res 18(6): 856-64, 2000.
Dennis et al., "In vivo anteroposterior femorotibial translation of total knee arthroplasty: a multicenter analysis," Clin Orthop Rel Res, 356: 47-57, 1998.
Clary et al., "Kinematics of Posterior Stabilized and Cruciate Retaining Knee Implants During an in Vitro Deep Knee Bend," 54th Annual Meeting of the Orthopaedic Research Society, Poster No. 1983, Mar. 2008.
Wang et al., "A biomechanical comparison between the single-axis and multi-axis total knee arthroplasty systems for stand-to-sit movement," Clin Biomech 20(4): 428-33, 2005.
Dennis et al., "Multicenter Determination of in Vivo Kinematics After Total Knee Arthroplasty," Clin. Orthop. Rel. Res., 416, 37-57, 21 pgs.
Yoshiya et al., "In Vivo Kinematic Comparison of Posterior Cruciate-Retaining and Posterior Stabilized Total Knee Arthroplasties Under Passive and Weight-bearing Conditions," J. Arthroplasty, vol. 20, No. 6, 2005, 7 pgs.
Bertin et al., "In Vivo Determination of Posterior Femoral Rollback for Subjects Having a NexGen Posterior Cruciate-Retaining Total Knee Arthroplasty," J. Arthroplasty, vol. 17, No. 8, 2002, 9 pgs.
Suggs et al., "Three-Dimensional Tibiofemoral Articular Contact Kinematics of a Cruciate-Retaining Total Knee Arthroplasty," JBJS-Am, vol. 88, No. 2, 2006, 10 pgs.
Dennis et al., "In Vivo Determination of Normal and Anterior Cruciate Ligament-Deficient Knee Kinematics," J. Biomechanics, 38, 241-253, 2005, 13 pgs.
Li et al., "Anterior Cruciate Ligament Deficiency Alters the in Vivo Motion of the Tibiofemoral Cartilage Contact Points in Both Anteroposterior and Mediolateral Directions," JBJS-Am, vol. 88, No. 8, Aug. 2006, 10 pgs.

Ries, "Effect of ACL Sacrifice, Retention, or Substitution on K After TKA," http://www.orthosupersite.com/view.asp?rID=23134, Aug. 2007, 5 pgs.
Ferris, "Matching observed spiral form curves to equations of spirals in 2-D images," The First Japanese-Australian Joint Seminar, 7 pgs.
Goodfellow et al., "The Mechanics of the Knee and Prosthesis Design," The Journal of Bone and Joint Surgery, vol. 60-B, No. 3, 12 pgs.
Dennis, et al. "A Multi-Center Analysis of Axial Femorotibial Rotation After Total Knee Arthoplasty", Clinical Orthopaedics 428 (2004); 180-189, 10 Pages.
Fan,Cheng-Yu, et al., "Primitive Results After Medical-Pivot Knee Arthroplasties: A Minimum 5 Year Follow-Up Study", The Journal of Arthroplasty, vol. 25, No. 3 2010, 492-496, 5 Pages.
Freeman, M.A.R., et al., "The Movement of the Normal Tibio-Femoral Joint", The Journal of Biomechanics 38 (2005) (2), pp. 197-208, 12 Pgs.
Fuller, et al., "A Comparison of Lower-Extremity Skeletal Kinematics Measured Using Skin and Pin-Mounted Markers", Human Movement Science 16 (1997) 219-242, 24 Pages.
Komistek, et al., "In Vivo Flouroscopic Analysis of the Normal Human Knee", Clinical Orthopaedics 410 (2003): 69-81, 13 Pages.
Mannan, et al., "The Medial Rotation Total Knee Replacement: A Clinical and Radiological Review at a Mean Follow-Up of Six Years", The Journal of Bone and Joint Surgery, vol. 91-B, No. 6 (Jun. 2009): 750-756, 7 Pages.
Shaw et al., "The Longitudinal Axis of the Knee and the Role of the Cruciate Ligaments in Controlling Transverse Rotation", J.Bone Joint Surg. AM. 1974:56:1603-1609, 8 Pages.
Extended European Search Report, European Application No. 10174440.7-1526, Dec. 10, 2010, 4 Pages.
Extended European Search Report, European Application No. 10174439.9-1526, Dec. 20, 2010, 4 Pages.
European search report; European Application No. 10174439.9-1526; Dec. 20, 2010; 4 pages.
European Search Report for European Patent Application No. 09164245A-2310, Oct. 15, 2009, 5 pgs.
European Search Report for European Patent Application No. 11150648.1-2310, Apr. 7, 2011, 5 pgs.
Kurosawa, et al., "Geometry and Motion of the Knee for Implant and Orthotic Design", The Journal of Biomechanics 18 (1985), pp. 487-499, 12 pages.
Barnes, C.L., et al, "Kneeling is Safe for Patients Implanted With Medical-Pivot Total Knee Arthroplasty Designs, Journal of Arthoplasty", vol. 00, No. 0 2010, 1-6, 6 pages.
Blaha, et al., "Kinematics of the Human Knee Using an Open Chain Cadaver Model", Clinical Orthopaedics and Related Research, vol. 410 (2003); 25-34, 10 pages.
Hill, et al., "Tibiofemoral Movement 2: The Loaded and Unloaded Living Knee Studied by MRI" The Journal of Bone & Joint Surgery, vol. 82-B, No. 8 (Nov. 2000), 1196-1198, 3 Pages.
Karachalios, et al., "A Mid-Term Clinical Outcome Study of the Advance Medial Pivot Knee Arthroplasty", www.sciencedirect.come, The Knee 16 (2009); 484-488, 5 pages.
Komistek, et al., "In Vivo Polyethylene Bearing Mobility is Maintained in Posterior Stabilized Total Knee Arthroplasty", Clinical Orthopaedics 428 (2004): 207-213, 7 pages.
Koo, et al., "The Knee Joint Center of Rotation is Predominantly on the Lateral Side During Normal Walking", Journal of Biomechanics, vol. 41 (2008): 1269-1273, 5 pages.
Moonot, et al., "Correlation Between the Oxford Knee and American Knee Society Scores at Mid-Term Follow-Up", The Journal of Knee Surgery, vol. 22, No. 3 (Jul. 2009), 226-230, 5 Pages.
Murphy, Michael Charles, "Geometry and the Kinematics of the Normal Human Knee", Submitted to Massachusetts Institute of Technology (1990), 379 Pages.
Nakagawa, et al., "Tibiofemoral Movement 3: Full Flexion of the Normal Human Knee", J.Bone Joint Surg. AM, vol. 82- B, No. 8 (2000). 1199-1200, 2 Pages.
Omori, et al., "The Effect of Geometry of the Tibial Polyethylene Insert on the Tibiofemoral Contact Kinematics in Advance Medical Pivot Total Knee Arthroplasty", The Journal of Orthopaedics Science (2009), 14:754-760, 7 pages.

(56) References Cited

OTHER PUBLICATIONS

Shakespeare, et al., "Flexion After Total Knee Replacement. A Comparison Between the Medical Pivot Knee and a Posterior Stabilised Knee", www.sciencedirect.com, The Knee 13 (2006): 371-372, 3 Pages.
Walker, et al., "Motion of a Mobile Bearing Knee Allowing Translation of Rotation", Journal of Arthroplasty 17 (2002): 11-19, 9 Pages.
European Patent Office, Search Report for App. No. 09164479.9-2310, mailed Nov. 4, 2009, 6 pages.
2nd Int'l Johnson-Elloy Knee Meeting, Mar. 1987, 9 pages.
Operative Technique, Johnson Elloy Knee System, Chas F. Thackray, Ltd., 1988, 34 pgs.
Operative Technique the Turning Point, Accord, the Johnson/Elloy Concept, Chas FL Thackray Ltd, 32 pages.
Restoration of Soft Tissue Stability, Johnson, et al., Chas. F. Thackray, Ltd., 21 pages.
The Turning Point, Accord, The Johnson Elloy Concept, Chas F. Thackray Ltd, 20 pages.
Prosthesis and Instrumentation the Turning Point, Accord, The Johnson/Elloy Concept, Chas F. Thackray Ltd, 8 pages.
Five to Eight Year Results of the Johnson/Elloy (Accord) Total Knee Arthroplasty, Johnson et al, The Journal of Arthroplasty, vol. 8, No. 1, Feb. 1993, 6 pages.
Factors Affecting the Range of Movement of Total Knee Arthroplasty, Harvey et al, The Journal of Bone and Joint Surgery, vol. 75-B, No. 6, Nov. 1993, 6 pages.
Advice Notice (NI) 2000/03, Defect & Investigation Centre, Mar. 13, 2000, 3 pages.
The Johnson Elloy (Accord) Total Knee Replacement, Norton et al, The Journal of Bone and Joint Surgery (BR), vol. 84, No. 6, Aug. 2002, 4 pages.
Midvatus Approach in Total Knee Arthroplasty, A Description and a Cadaveric Study Determining the Distance of the Popliteal Artery From the Patellar Margin of the Incision, Cooper et al., The Journal of Arthroplasty, vol. 14 No. 4, 1999, 4 pages.
European Search Report for European Patent Application No. 08164944.4-2310-2042131, Mar. 16, 2009, 12 pgs.
Biomet, Vanguard Mono-Lock Tibial System, Patented Convertible Tibial Bearing Technology, 2009, 2 Pages.
Cari Zeiss, Zeiss Surfcomm 5000—"Contour and Surface Measuring Machines", 2005, 16 pages.
DePuy Inc., "AMK Total Knee System Product Brochure", 1996, 8 pages.
DePuy Knees International, "Sigma CR Porocoat.RTM.," 1 page.
DePuy Orthopaedics, Inc., "AMK Total Knee System Legent II Surgical Techinque", 1998, 30 pages.
DePuy Orthopaedics, Inc., "Sigma Fixed Bearing Knees—Function with Wear Resistance", 2010, 0612-65-508 (Rev. 1) 20 pages.
DePuy PFC Sigma RP, "PFC Sigma Knee System with Rotating Platform Technical Monograph", 1999, 0611-29-050 (Rev. 3), 70 pages.
Effects of Coronal Plane Conformity on Tibial Loading in TKA: A Comparison of AGC Flat Versus Conforming Articulations, Brent, et al, Orthopaedic Surgery, Surgical Technology International, XVIII, 6 pages.
European Search Report for European Patent Application No. 08253140.1-2310, Dec. 23, 2008, 7 pgs.
European Search Report for European Patent Application No. 06739287.8-2310, Mar. 16, 2010, 3 Pages.
European Search Report for European Patent Application No. 09164478.1-2310, Oct. 20, 2009, 6 Pages.
European Search Report for European Patent Application No. 09164478.1-2310, Apr. 28, 2010, 12 Pages.
European Search Report for European Patent Application No. 10162138.1, Aug. 30, 2010, 7 Pages.
Japanese Search Report for Japanese Patent Application No. 2009-501393, Oct. 26, 2010, 5 Pages.
PCT Notification Concerning Transmittal of International Prel. Report for Corresponding International App. No. PCT/US2006/010431, Jun. 5, 2007, 89 Pages.
Procedure, References Guide for Use with P.F.C. Sigma Knee Systems, 1998, 8 pages.
The Effects of Conformity and Load in Total Knee Replacement, Kuster, et al, Clinical Orthopaedics and Related Research No. 375, Jun. 2000.
Zimmer Nexgen Trabecular Metal Tibial Tray, The Best Thing Next to Bone, 97-5954-001-00, 2007, 4 pages.
Zimmer, Trabecular Metal Monoblock Tibial Components, An Optimal Combination of Material and Design, www.zimmer.com, 2009, 3 pages.
European Seach Report for European Patent Application No. 09164235.5-1526, Dec. 22, 2009, 6 pgs.
Signus Medizintechnik, "Peek-Optima.Rtm., The Polymer for Implants, Technical Information for the Medical Professional", 7 pages.
The Accuracy of Intramedullary Alignment in Total Knee Replacement, Elloy, et al, Chas F. Thackray Ltd, 12 pages.
PCT Notification concerning transmittal of International Preliminary Report for corresponding International Appl. No. PCT/US2006/010431, Dec. 2, 2008, 6 pages.
State Intellectual Property Office of People's Republic China; Chinese Search Report; Application No. 200910166935.6; Mar. 26, 2013; 2 pages.
PCT Written Opinion of the International Searching Authority for Corresponding International App. Search Report PCT/US 12/44354, Sep. 24, 2012, 11 pages.

| Component Size | Origin Distance | RAY LENGTH EQUATION |
|---|---|---|
| 1 | 4.008 | R=29.383391+0.016694187*θ−0.000270002378*θ²−0.0000124837*θ³ |
| 2 | 3.898 | R=30.470577+0.016694187*θ−0.000270002378*θ²−0.0000124837*θ³ |
| 3 | 3.722 | R=31.597988+0.016694187*θ−0.000270002378*θ²−0.0000124837*θ³ |
| 4 | 3.629 | R=32.767114+0.016694187*θ−0.000270002378*θ²−0.0000124837*θ³ |
| 5 | 3.468 | R=33.979497+0.016694187*θ−0.000270002378*θ²−0.0000124837*θ³ |
| 6 | 3.288 | R=35.236738+0.016694187*θ−0.000270002378*θ²−0.0000124837*θ³ |
| 7 | 3.088 | R=36.540498+0.016694187*θ−0.000270002378*θ²−0.0000124837*θ³ |
| 8 | 2.866 | R=37.892496+0.016694187*θ−0.000270002378*θ²−0.0000124837*θ³ |
| 9 | 2.623 | R=39.294518+0.016694187*θ−0.000270002378*θ²−0.0000124837*θ³ |
| 10 | 2.356 | R=40.748416+0.016694187*θ−0.000270002378*θ²−0.0000124837*θ³ |

| Component Size | R1 | R2 | R3 | R4 | R5 | Ratio R1/R2 | Ratio R1/R3 | Ratio R1/R4 |
|---|---|---|---|---|---|---|---|---|
| 1 | 25.5 | 20.4 | 25.4 | 11.2 | 8.1 | 1.251 | 1.005 | 2.271 |
| 2 | 26.7 | 21.3 | 26.6 | 12.6 | 7.9 | 1.252 | 1.005 | 2.120 |
| 3 | 28.0 | 22.3 | 27.8 | 14.0 | 7.7 | 1.253 | 1.005 | 2.001 |
| 4 | 29.3 | 23.3 | 29.1 | 15.4 | 7.5 | 1.255 | 1.005 | 1.901 |
| 5 | 30.7 | 24.4 | 30.5 | 16.9 | 7.3 | 1.257 | 1.005 | 1.818 |
| 6 | 32.1 | 25.5 | 31.9 | 18.4 | 7.1 | 1.259 | 1.005 | 1.747 |
| 7 | 33.6 | 26.7 | 33.4 | 19.9 | 6.8 | 1.261 | 1.005 | 1.686 |
| 8 | 35.2 | 27.9 | 35.0 | 21.5 | 6.6 | 1.263 | 1.005 | 1.633 |
| 9 | 36.8 | 29.1 | 36.7 | 23.2 | 6.3 | 1.265 | 1.005 | 1.586 |
| 10 | 38.6 | 30.4 | 38.4 | 25.0 | 6.1 | 1.268 | 1.005 | 1.545 |

ORTHOPAEDIC KNEE PROSTHESIS HAVING CONTROLLED CONDYLAR CURVATURE

This application is a continuation of Utility patent application Ser. No. 13/481,943, now U.S. Pat. No. 8,834,575, entitled "Posterior Stabilized Orthopaedic Knee Prosthesis Having Controlled Condylar Curvature" by Joseph G. Wyss, which was filed on May 28, 2012, which was a continuation of U.S. patent application Ser. No. 12/165,575, now U.S. Pat. No. 8,187,335, which was filed on Jun. 30, 2008, the entirety of each of which is hereby incorporated by reference.

CROSS-REFERENCE TO RELATED U.S. PATENT APPLICATION

Cross-reference is made to U.S. Utility patent application Ser. No. 12/165,579 now U.S. Pat. No. 8,828,086 entitled "Orthopaedic Femoral Component Having Controlled Condylar Curvature" by John L. Williams et al., which was filed on Jun. 30, 2008; to U.S. Utility patent application Ser. No. 12/165,574, now U.S. Pat. No. 8,192,498 entitled "Posterior Cruciate-Retaining Orthopaedic Knee Prosthesis Having Controlled Condylar Curvature" by Christel M. Wagner, which was filed on Jun. 30, 2008; to U.S. Utility patent application Ser. No. 12/165,582, now U.S. Pat. No. 8,206,451 entitled "Posterior Stabilized Orthopaedic Prosthesis" by Joseph G. Wyss, which was filed on Jun. 30, 2008; and to U.S. Provisional Patent Application Ser. No. 61/077,124 entitled "Orthopaedic Knee Prosthesis Having Controlled Condylar Curvature" by Joseph G. Wyss, which was filed on Jun. 30, 2008; the entirety of each of which is incorporated herein by reference.

TECHNICAL FIELD

The present disclosure relates generally to orthopaedic prostheses, and particularly to orthopaedic prostheses for use in knee replacement surgery.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. Depending on the severity of the damage to the patient's joint, orthopaedic prostheses of varying mobility may be used. For example, the knee prosthesis may include a "fixed" tibial bearing in cases wherein it is desirable to limit the movement of the knee prosthesis, such as when significant soft tissue damage or loss is present. Alternatively, the knee prosthesis may include a "mobile" tibial bearing in cases wherein a greater degree of freedom of movement is desired. Additionally, the knee prosthesis may be a total knee prosthesis designed to replace the femoral-tibial interface of both condyles of the patient's femur or a uni-compartmental (or uni-condylar) knee prosthesis designed to replace the femoral-tibial interface of a single condyle of the patient's femur.

The type of orthopedic knee prosthesis used to replace a patient's natural knee may also depend on whether the patient's posterior cruciate ligament is retained or sacrificed (i.e., removed) during surgery. For example, if the patient's posterior cruciate ligament is damaged, diseased, and/or otherwise removed during surgery, a posterior stabilized knee prosthesis may be used to provide additional support and/or control at later degrees of flexion. Alternatively, if the posterior cruciate ligament is intact, a cruciate retaining knee prosthesis may be used.

Typical orthopaedic knee prostheses are generally designed to duplicate the natural movement of the patient's joint. As the knee is flexed and extended, the femoral and tibial components articulate and undergo combinations of relative anterior-posterior motion and relative internal-external rotation. However, the patient's surrounding soft tissue also impacts the kinematics and stability of the orthopaedic knee prosthesis throughout the joint's range of motion. That is, forces exerted on the orthopaedic components by the patient's soft tissue may cause unwanted or undesirable motion of the orthopaedic knee prosthesis. For example, the orthopaedic knee prosthesis may exhibit an amount of unnatural (paradoxical) anterior translation as the femoral component is moved through the range of flexion.

In a typical orthopaedic knee prosthesis, paradoxical anterior translation may occur at nearly any degree of flexion, but particularly at mid to late degrees of flexion. Paradoxical anterior translation can be generally defined as an abnormal relative movement of a femoral component on a tibial bearing wherein the contact "point" between the femoral component and the tibial bearing "slides" anteriorly with respect to the tibial bearing. This paradoxical anterior translation may result in loss of joint stability, accelerated wear, abnormal knee kinematics, and/or cause the patient to experience a sensation of instability during some activities.

SUMMARY

According to one aspect, a posterior stabilized orthopaedic knee prosthesis includes a femoral component and a tibial bearing. The femoral component may include a pair of spaced apart condyles defining an intracondylar notch therebetween. At least one of the pair of spaced apart condyles may have a condyle surface curved in the sagittal plane. The femoral component may also include a posterior cam positioned in the intracondylar notch. The tibial bearing may include a platform having a bearing surface configured to articulate with the condyle surface of the femoral component and a spine extending upwardly from the platform.

In some embodiments, the condyle surface of the femoral component may contact the bearing surface at a first contact point on the condyle surface at a first degree of flexion, contact the bearing surface at a second contact point on the condyle surface at a second degree of flexion, and contact the bearing surface at a third contact point on the condyle surface at a third degree of flexion. Additionally, the posterior cam of the femoral component may contact the spine of the tibial bearing at a fourth degree of flexion.

The second degree of flexion may be greater than the first degree of flexion and may be in the range of about 0 degrees to about 50 degrees in some embodiments. For example, in one embodiment, the second degree of flexion is no greater than about 30 degrees. The third degree of flexion may be greater than the second degree and less than about 90 degrees. For example, in one embodiment, the third degree of flexion is at least 30 degrees. In another embodiment, the third degree of flexion is at least 50 degrees. In still another embodiment, the third degree of flexion is at least 70 degrees. In some embodiments, the fourth degree of flexion is no greater than about 10 degrees more than the third degree of flexion. For example, in one particular embodiment, the fourth degree of flexion is no greater than the third degree of flexion. Additionally, in some embodiments, the fourth degree of flexion is at least 50 degrees. In another embodiment, the fourth degree of flexion is at least 70 degrees.

The condyle surface in the sagittal plane may have a first radius of curvature at the first contact point, a second radius of curvature at the second contact point, and a third radius of curvature at the third contact point. In some embodiments, the third radius of curvature is greater than the second radius of curvature by at least 0.5 millimeters. For example, the third radius of curvature may be greater than the second radius of curvature by at least 2 millimeters in some embodiments or 5 millimeters in other embodiments. Additionally, in some embodiments, the ratio of the second radius to the third radius is in the range of 0.75 to 0.85.

In some embodiments, the condyle surface of the femoral component in the sagittal plane may include first curved surface section and a second curved surface section. The first curved surface section may be defined between the first contact point and the second contact point. The second curved surface section may be defined between the second contact point and the third contact point. In such embodiments, the first curved surface section may have a substantially constant radius of curvature substantially equal to the second radius of curvature. Additionally, the second curved surface section may have a substantially constant radius of curvature substantially equal to the third radius of curvature.

According to another aspect, a posterior stabilized orthopaedic knee prosthesis includes a femoral component and a tibial bearing. The femoral component may include a pair of spaced apart condyles defining an intracondylar notch therebetween. At least one of the pair of spaced apart condyles may have a condyle surface curved in the sagittal plane. The femoral component may also include a posterior cam positioned in the intracondylar notch. The tibial bearing may include a platform having a bearing surface configured to articulate with the condyle surface of the femoral component and a spine extending upwardly from the platform.

In some embodiments, the condyle surface of the femoral component may contact the bearing surface at a first contact point on the condyle surface at a first degree of flexion. The first degree of flexion may be less than about 30 degrees. Additionally, the condyle surface may contact the bearing surface at a second contact point on the condyle surface at a second degree of flexion. The second degree of flexion may be in the range of 35 degrees to 90 degrees. The condyle surface of the femoral component may also contact the bearing surface at a third contact point on the condyle surface at a third degree of flexion. The third degree of flexion may be greater than the second degree of flexion. Additionally, the condyle surface may contact the bearing surface at a plurality of contact points between the first contact point and the second contact point when the femoral component is moved from the first degree of flexion to the second degree of flexion. Further, in some embodiments, the posterior cam of the femoral component may contact the spine of the tibial bearing at a fourth degree of flexion. The fourth degree of flexion at which the posterior cam contacts the spine may be less than, substantially equal to, or slightly greater than the third degree of flexion. For example, in one embodiment, the fourth degree of flexion is no greater than about 10 degrees more than the third degree of flexion.

In some embodiments, each contact point of the plurality of contact points is defined by a ray extending from a common origin to the respective contact point of the plurality of contact points. Each ray has a length defined by the following polynomial equation: $r_\theta = (a + (b*\theta) + (c*\theta^2) + (d*\theta^3))$, wherein $r_\theta$ is the length of the ray defining a contact point at $\theta$ degrees of flexion, a is a coefficient value between 20 and 50, and b is a coefficient value in a range selected from the group consisting of: $-0.30 < b < 0.0$, $0.00 < b < 0.30$, and $b = 0$. If b is in the range of $-0.30 < b < 0.00$, then c is a coefficient value between 0.00 and 0.012 and d is a coefficient value between $-0.00015$ and 0.00. Alternatively, if b is in the range of $0 < b < 0.30$, then c is a coefficient value between $-0.010$ and 0.00 and d is a coefficient value between $-0.00015$ and 0.00. Alternatively still, if b is equal to 0, then c is a coefficient value in a range selected from the group consisting of: $-0.0020 < c < 0.00$ and $0.00 < c < 0.0025$ and d is a coefficient value between $-0.00015$ and 0.00. In some embodiments, the distance between the origin of the first radius of curvature and the common origin of the rays is in the range of 0 and 10 millimeters.

In some embodiments, the first degree of flexion may be in the range of 0 degrees to 10 degrees, the second degree of flexion may be in the range of 45 degrees to 55 degrees, and the third degree of flexion may be in the range of about 65 degrees to about 75 degrees. For example, in one particular embodiment, the first degree of flexion is about 0 degrees, the second degree of flexion is about 50 degrees, and the third degree of flexion is about 70 degrees. Additionally, the fourth degree of flexion may be about 70 degrees.

In some embodiments, the condyle surface in the sagittal plane has a first radius of curvature at the first contact point, a second radius of curvature at the second contact point, and a third radius of curvature at the third radius of curvature. In such embodiments, the third radius of curvature is greater than the second radius of curvature by at least 0.5 millimeters. In some embodiments, the third radius of curvature may be greater than the first radius of curvature by at least 2 millimeters. Additionally, in some embodiments, the third radius of curvature is greater than the first radius of curvature by at least 5 millimeters.

Additionally, in some embodiments, the condyle surface of the femoral component in the sagittal plane may include a curved surface section defined between the second contact point and the third contact point. In such embodiments, the curved surface section may have a substantially constant radius of curvature substantially equal to the third radius of curvature.

According to yet another aspect, a posterior stabilized orthopaedic knee prosthesis may include a posterior stabilized orthopaedic knee prosthesis includes a femoral component and a tibial bearing. The femoral component may include a pair of spaced apart condyles defining an intracondylar notch therebetween. At least one of the pair of spaced apart condyles may have a condyle surface curved in the sagittal plane. The femoral component may also include a posterior cam positioned in the intracondylar notch. The tibial bearing may include a platform having a bearing surface configured to articulate with the condyle surface of the femoral component and a spine extending upwardly from the platform.

In some embodiments, the condyle surface of the femoral component may contact the bearing surface at a first contact point on the condyle surface at a first degree of flexion. The first degree of flexion may be less than about 30 degrees. Additionally, the condyle surface may contact the bearing surface at a second contact point on the condyle surface at a second degree of flexion. The second degree of flexion may be in the range of 35 degrees to 90 degrees. The condyle surface of the femoral component may also contact the bearing surface at a third contact point on the condyle surface at a third degree of flexion. The third degree of flexion may be greater than the second degree of flexion. In some embodiments, the posterior cam of the femoral component may contact the spine of the tibial bearing at a fourth degree of flexion. Additionally, the condyle surface may contact the bearing surface at a plurality of contact points between the first contact point and the second contact point when the femoral component is moved from the first degree of flexion to the second degree of flexion. Further, in some embodiments, the posterior cam of the femoral component may contact the spine of the tibial bearing at a fourth degree of flexion. The fourth degree of flexion may be equal to or less than the third degree of flexion.

In some embodiments, the condyle surface in the sagittal plane has a first radius of curvature at the first contact point, a second radius of curvature at the second contact point, and a third radius of curvature at the third radius of curvature. In such embodiments, the third radius of curvature is greater than the second radius of curvature by at least 2.0 millimeters.

Yet further, each contact point of the plurality of contact points may be defined by a ray extending from a common origin to the respective contact point of the plurality of contact points. Each ray has a length defined by the following polynomial equation: $r_\theta=(a+(b*\theta)+(c*\theta^2)+(d*\theta^3))$, wherein $r_\theta$ is the length of the ray defining a contact point at 0 degrees of flexion, a is a coefficient value between 20 and 50, and b is a coefficient value in a range selected from the group consisting of: $-0.30<b<0.0$, $0.00<b<0.30$, and $b=0$. If b is in the range of $-0.30<b<0.00$, then c is a coefficient value between 0.00 and 0.012 and d is a coefficient value between $-0.00015$ and 0.00. Alternatively, if b is in the range of $0<b<0.30$, then c is a coefficient value between $-0.010$ and 0.00 and d is a coefficient value between $-0.00015$ and 0.00. Alternatively still, if b is equal to 0, then c is a coefficient value in a range selected from the group consisting of: $-0.0020<c<0.00$ and $0.00<c<0.0025$ and d is a coefficient value between $-0.00015$ and 0.00. In some embodiments, the distance between the origin of the first radius of curvature and the common origin of the rays is in the range of 0 and 10 millimeters.

Additionally, in some embodiments, each of the pair of spaced apart condyles may include a condyle surface. In such embodiments, the condyle surfaces may be substantially symmetrical or may be asymmetrical.

BRIEF DESCRIPTION OF THE DRAWINGS

The detailed description particularly refers to the following figures, in which:

FIG. 14 is a table of one embodiment of coefficient values of a polynomial equation defining the curve of the femoral component of FIG. 13 for a family of femoral component sizes;

DETAILED DESCRIPTION OF THE DRAWINGS

Figure 1:
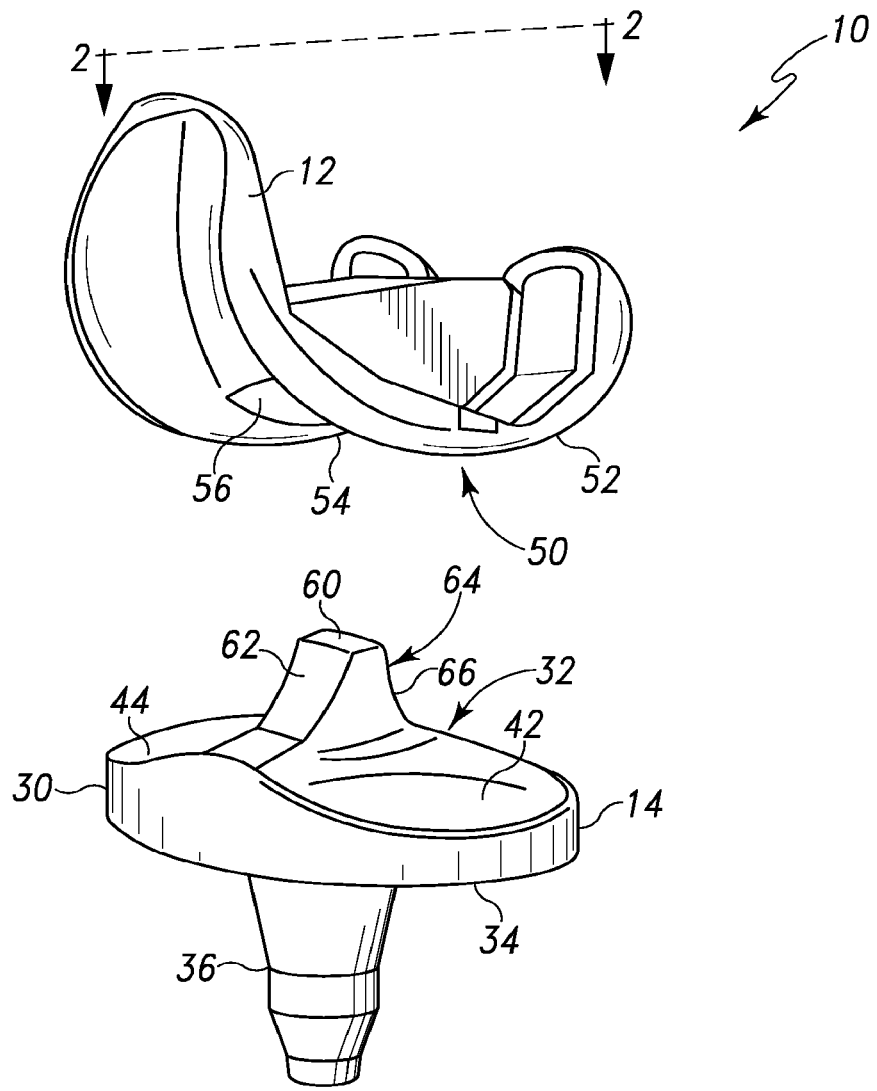
FIG. 1 is an exploded perspective view of one embodiment of an orthopaedic knee prosthesis.
Figure 1:
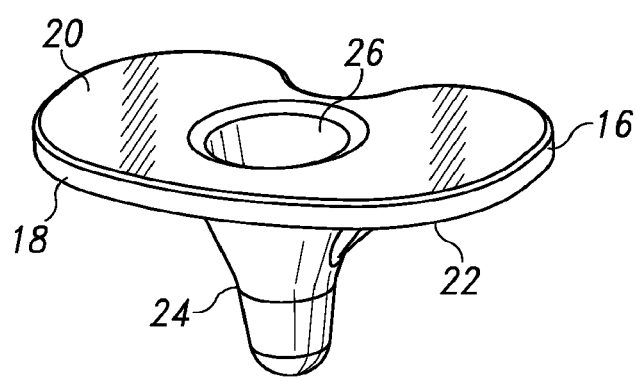

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIG. 1, in one embodiment, a posterior stabilized orthopaedic knee prosthesis 10 includes a femoral component 12, a tibial bearing 14, and a tibial tray 16. The femoral component 12 and the tibial tray 16 are illustratively formed from a metallic material such as cobalt-chromium or titanium, but may be formed from other materials, such as a ceramic material, a polymer material, a bio-engineered material, or the like, in other embodiments. The tibial bearing 14 is illustratively formed from a polymer material such as a ultra-high molecular weight polyethylene (UHMWPE), but may be formed from other materials, such as a ceramic material, a metallic material, a bio-engineered material, or the like, in other embodiments.

As discussed in more detail below, the femoral component 12 is configured to articulate with the tibial bearing 14, which is configured to be coupled with the tibial tray 16. The illustrative tibial bearing 14 is embodied as a rotating or mobile tibial bearing and is configured to rotate relative to the tibial tray 12 during use. However, in other embodiments, the tibial bearing 14 may be embodied as a fixed tibial bearing, which may be limited or restricted from rotating relative the tibial tray 16.

The tibial tray 16 is configured to be secured to a surgically-prepared proximal end of a patient's tibia (not shown). The tibial tray 16 may be secured to the patient's tibia via use of bone adhesive or other attachment means. The tibial tray 16 includes a platform 18 having an top surface 20 and a bottom surface 22. Illustratively, the top surface 20 is generally planar and, in some embodiments, may be highly polished. The tibial tray 16 also includes a stem 24 extending downwardly from the bottom surface 22 of the platform 18. A cavity or bore 26 is defined in the top surface 20 of the platform 18 and extends downwardly into the stem 24. The bore 26 is formed to receive a complimentary stem of the tibial insert 14 as discussed in more detail below.

As discussed above, the tibial bearing 14 is configured to be coupled with the tibial tray 16. The tibial bearing 14 includes a platform 30 having an upper bearing surface 32 and a bottom surface 34. In the illustrative embodiment wherein the tibial bearing 14 is embodied as a rotating or mobile tibial bearing, the bearing 14 includes a stem 36 extending downwardly from the bottom surface 32 of the platform 30. When the tibial bearing 14 is coupled to the tibial tray 16, the stem 36 is received in the bore 26 of the tibial tray 16. In use, the tibial bearing 14 is configured to rotate about an axis defined by the stem 36 relative to the tibial tray 16. In embodiments wherein the tibial bearing 14 is embodied as a fixed tibial bearing, the bearing 14 may or may not include the stem 36 and/or may include other devices or features to secure the tibial bearing 14 to the tibial tray 18 in a non-rotating configuration.

The upper bearing surface 32 of the tibial bearing 14 includes a medial bearing surface 42, a lateral bearing surface 44, and a spine 60 extending upwardly from the platform 16. The medial and lateral bearing surfaces 42, 44 are configured to receive or otherwise contact corresponding medial and lateral condyles 52, 54 of the femoral component 14 as discussed in more detail below. As such, each of the bearing surface 42, 44 has a concave contour. The spine 60 is positioned between the bearing surfaces 42, 44 and includes an anterior side 62 and a posterior side 64 having a cam surface 66. In the illustrative embodiment, the cam surface 66 has a substantially concave curvature. However, spines 60 including cam surfaces 66 having other geometries may be used in other embodiments. For example, a tibial bearing including a spine having a substantially "S"-shaped cross-sectional profile, such as the tibial bearing described in U.S. patent application Ser. No. 13/527,758, entitled "Posterior Stabilized Orthopaedic Prosthesis" by Joseph G. Wyss, et al., which is hereby incorporated by reference, may be used in other embodiments.

The femoral component 12 is configured to be coupled to a surgically-prepared surface of the distal end of a patient's femur (not shown). The femoral component 12 may be secured to the patient's femur via use of bone adhesive or other attachment means. The femoral component 12 includes an outer, articulating surface 50 having a pair of medial and lateral condyles 52, 54. In use, the condyles 52, 54 replace the natural condyles of the patient's femur and are configured to articulate on the corresponding bearing surfaces 42, 44 of the platform 30 of the tibial bearing 14.

The condyles 52, 54 are spaced apart to define an intracondyle notch or recess 56 therebetween. A posterior cam 80 and an anterior cam 82 (see FIG. 2) are positioned in the intracondyle notch 56. The posterior cam 80 is located toward the posterior side of the femoral component 12 and includes a cam surface 86 is configured to engage or otherwise contact the cam surface 66 of the spine 60 of the tibial bearing 12 during flexion as illustrated in and described in more detail below in regard to FIGS. 2-4.

It should be appreciated that the illustrative orthopaedic knee prosthesis 10 is configured to replace a patient's right knee and, as such, the bearing surface 42 and the condyle 52 are referred to as being medially located; and the bearing surface 44 and the condyle 54 are referred to as being laterally located. However, in other embodiments, the orthopaedic knee prosthesis 10 may be configured to replace a patient's left knee. In such embodiments, it should be appreciated that the bearing surface 42 and the condyle 52 may be laterally located and the bearing surface 44 and the condyle 54 may be medially located. Regardless, the features and concepts described herein may be incorporated in an orthopaedic knee prosthesis configured to replace either knee joint of a patient.

Figure 2:
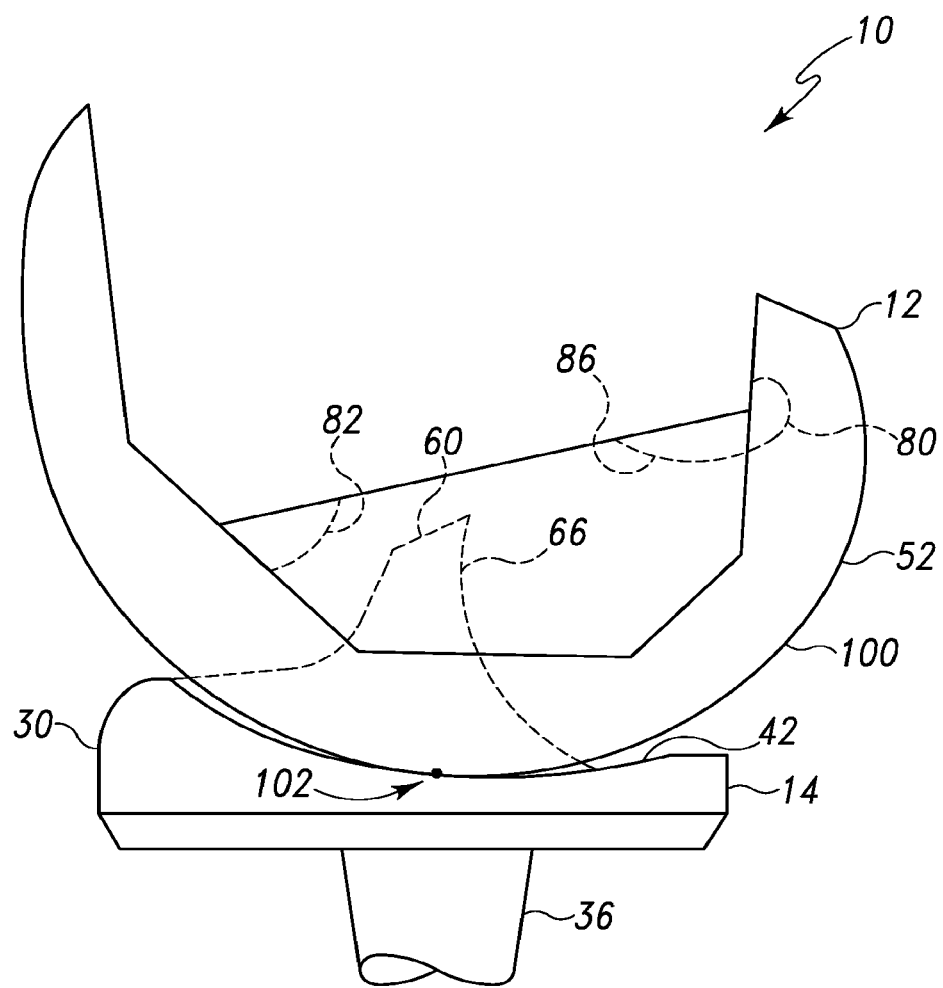
FIG. 2 is a cross-sectional view of a femoral component and tibial bearing of FIG. 1 taken generally along section lines 2-2 and having the femoral component articulated to a first degree of flexion.
Figure 3:
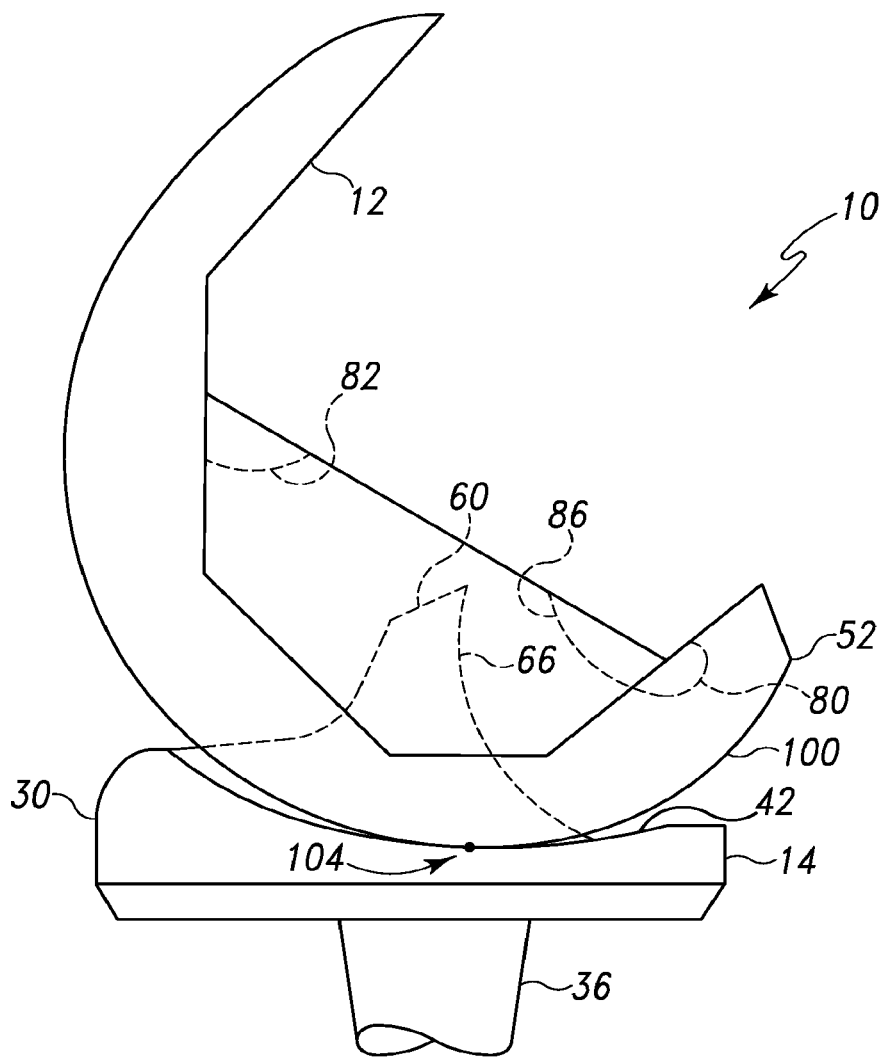
FIG. 3 is a cross-sectional view of a femoral component and tibial bearing of FIG. 2 having the femoral component articulated to a second degree of flexion.
Figure 4:
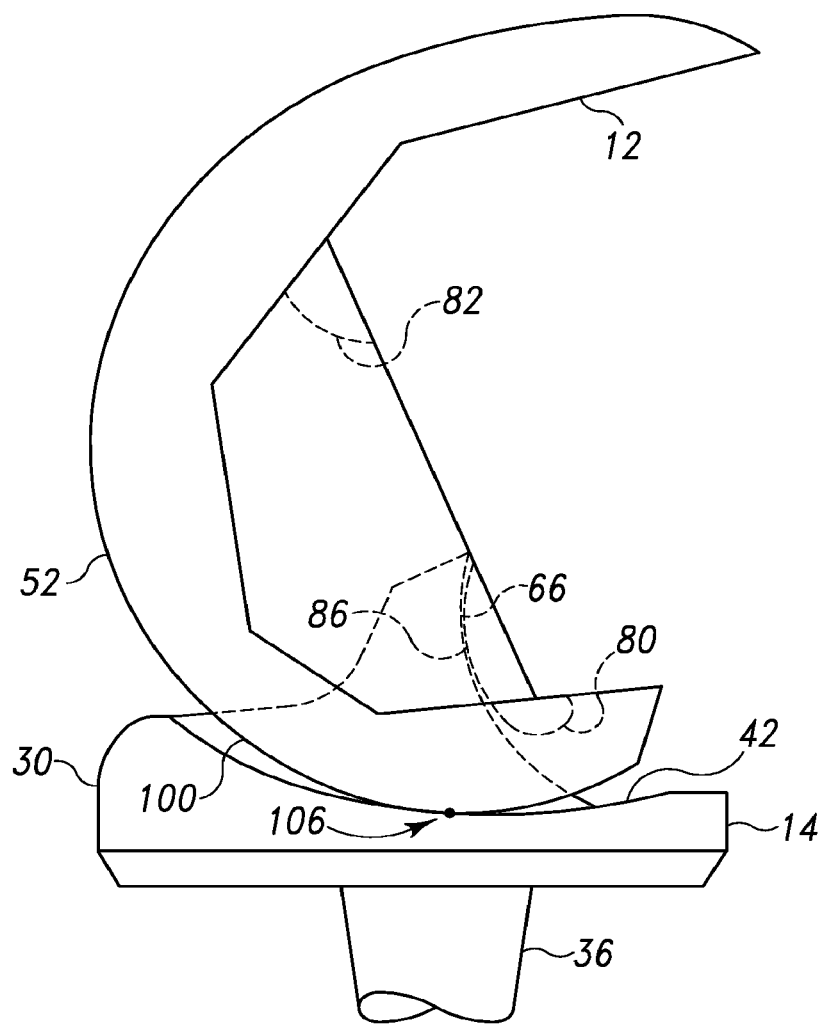
FIG. 4 is a cross-sectional view of a femoral component and tibial bearing of FIG. 2 having the femoral component articulated to a third degree of flexion.

Referring now to FIGS. 2-4, the femoral component 12 is configured to articulate on the tibial bearing 14 during use. Each condyle 52, 54 of the femoral component 12 includes a condyle surface 100, which is convexly curved in the sagittal plane and configured to contact the respective bearing surface 42, 44. Additionally, during a predetermined range of flexion, the posterior cam 80 of the femoral component 12 contacts the spine 60 of the tibial bearing 14. For example, in one embodiment as shown in FIG. 2, when the orthopaedic knee prosthesis 10 is in extension or is otherwise not in flexion (e.g., a flexion of about 0 degrees), the condyle surface 100 of the condyle 52 contacts the bearing surface 42 (or bearing surface 44 in regard to condyle 54) at one or more contact points 100 on the condyle surface 100. Additionally, at this particular degree of flexion, the posterior cam 80 is not in contact with the spine 60. However, at later (i.e., larger) degrees of flexion, the posterior cam 80 is configured to contact the spine 60 to provide an amount of control over the kinematics of the orthopaedic prosthesis.

As the orthopaedic knee prosthesis 10 is articulated through the middle degrees of flexion, the femoral component 12 contacts the tibial bearing 14 at one or more contact points on the condyle surface 100. For example, in one embodiment as illustrated in FIG. 3, when the orthopaedic knee prosthesis 10 is articulated to a middle degree of flexion (e.g., at about 45 degrees), the condyle surface 100 contacts the bearing surface 42 at one or more contact points 104 on the condyle surface 100. As discussed in more detail below, depending on the particular embodiment, the posterior cam 80 may or may not be in contact with the spine 60 at this particular degree of flexion. Regardless, as the orthopaedic knee prosthesis 10 is articulated to a late degree of flexion (e.g., at about 70 degrees of flexion), the condyle surface 100 contacts the bearing surface 42 at one or more contact points 106 on the condyle surface 100 as illustrated in FIG. 4. Additionally, the posterior cam 80 is now in contact with the spine 60. It should be appreciated, of course, that the femoral component 12 may contact the tibial bearing 14 at a plurality of contact points on the condyle surface 100 at any one particular degree of flexion. However, for clarity of description, only the contact points 102, 104, 106 have been illustrated in FIGS. 2-4, respectively.

The particular degree of flexion at which the posterior cam 80 initially contacts the spine 60 is based on the particular geometry of the condyle surface 100 of the femoral component 12. For example, in the illustrative embodiment of FIGS. 2-4, the orthopaedic knee prosthesis 10 is configured such that the posterior cam 80 initially contacts the spine 60 at about 70 degrees of flexion. However, in other embodiments the posterior cam 80 may initially contact the spine 60 at other degrees of flexion as discussed in more detail below.

The orthopaedic knee prosthesis 10 is configured such that the amount of paradoxical anterior translation of the femoral component 12 relative to the tibial bearing 14 may be reduced or otherwise delayed to a later (i.e., larger) degree of flexion. In particular, as discussed in more detail below, the condyle surface 100 of one or both of the condyles 52, 54 has particular geometry or curvature configured to reduce and/or delay anterior translations and, in some embodiments, promote "roll-back" or posterior translation, of the femoral component 12. It should be appreciated that by delaying the onset of paradoxical anterior translation of the femoral component 12 to a larger degree of flexion, the overall occurrence of paradoxical anterior translation may be reduced during those activities of a patient in which deep flexion is not typically obtained.

In a typical orthopaedic knee prosthesis, paradoxical anterior translation may occur whenever the knee prosthesis is positioned at a degree of flexion greater than zero degrees. The likelihood of anterior translation generally increases as the orthopaedic knee prosthesis is articulated to larger degrees of flexion, particularly in the mid-flexion range. In such orientations, paradoxical anterior translation of the femoral component on the tibial bearing can occur whenever the tangential (traction) force between the femoral component and the tibial bearing fails to satisfy the following equation:

$$T < \mu N \quad (1)$$

wherein "T" is the tangential (traction) force, "μ" is the coefficient of friction of the femoral component and the tibial bearing, and "N" is the normal force between the femoral component and the tibial bearing. As a generalization, the tangential (traction) force between the femoral component and the tibial bearing can be defined as $$T = M/R \quad (2)$$

wherein "T" is the tangential (traction) force between the femoral component and the tibial bearing, "M" is the knee moment, and "R" is the radius of curvature in the sagittal plane of the condyle surface in contact with the tibial bearing at the particular degree of flexion. It should be appreciated that equation (2) is a simplification of the governing real-world equations, which does not consider such other factors as inertia and acceleration. Regardless, the equation (2) provides insight that paradoxical anterior translation of an orthopaedic knee prosthesis may be reduced or delayed by controlling the radius of curvature of the condyle surface of the femoral component. That is, by controlling the radius of curvature of the condyle surface (e.g., increasing or maintaining the radius of curvature), the right-hand side of equation (2) may be reduced, thereby decreasing the value of the tangential (traction) force and satisfying the equation (1). As discussed above, by ensuring that the tangential (traction) force satisfies equation (1), paradoxical anterior translation of the femoral component on the tibial bearing may be reduced or otherwise delayed to a greater degree of flexion.

Based on the above analysis, to reduce or delay the onset of paradoxical anterior translation, the geometry of the condyle surface 100 of one or both of the condyles 52, 54 of the femoral component 12 is controlled. For example, in some embodiments, the radius of curvature of the condyle surface 100 is controlled such that the radius of curvature is held constant over a range of degrees of flexion and/or is increased in the early to mid flexion ranges. Comparatively, typical femoral components have decreasing radii of curvatures beginning at the distal radius of curvature (i.e., at about 0 degrees of flexion). However, it has been determined that by maintaining a relatively constant radius of curvature (i.e., not decreasing the radius of curvature) over a predetermined range of degrees of early to mid-flexion and/or increasing the radius of curvature over the predetermined range of degrees of flexion may reduce or delay paradoxical anterior translation of the femoral component 12.

Additionally, in some embodiments, the condyle surface 100 is configured or designed such that the transition between discrete radii of curvature of the condyle surface 100 is gradual. That is, by gradually transitioning between the discrete radii of curvature, rather than abrupt transitions, paradoxical anterior translation of the femoral component 12 may be reduced or delayed. Further, in some embodiments, the rate of change in the radius of curvature of the condyle surface in the early to mid flexion ranges (e.g., from about 0 degrees to about 90 degrees) is controlled such that the rate of change is less than a predetermined threshold. That is, it has been determined that if the rate of change of the radius of curvature of the condyle surface 100 is greater than the predetermined threshold, paradoxical anterior translation may occur.

Accordingly, in some embodiments as illustrated in FIGS. 5-8, the condyle surface 100 of the femoral component 12 has an increased radius of curvature in early to middle degrees of flexion. By increasing the radius of curvature, paradoxical anterior translation may be reduced or delayed to a later degree of flexion as discussed in more detail below. In particular, paradoxical anterior translation may be delayed to a degree of flexion at or beyond which the posterior cam 80 of the femoral component 12 initially contacts the spine 60 of the tibial bearing 14. Once the posterior cam 80 is in contact with the spine 60, paradoxical anterior translation is controlled by the engagement of the posterior cam 80 to the spine 60. That is, the posterior cam 80 may be restricted from moving anteriorly by the spine 60.

The amount of increase between the radius of curvature R2 and the radius of curvature R3, as well as, the degree of flexion on the condyle surface 100 at which such increase occurs has been determined to affect the occurrence of paradoxical anterior translation. As discussed in more detail in the U.S. patent application Ser. No. 12/165,579, entitled "Orthopaedic Femoral Prosthesis Having Controlled Condylar Curvature", which was filed concurrently herewith and is hereby incorporated by reference, multiple simulations of various femoral component designs were performed using the LifeMOD/Knee Sim, version 1007.1.0 Beta 16 software program, which is commercially available from LifeModeler, Inc. of San Clemente, Calif., to analyze the effect of increasing the radius of curvature of the condyle surface of the femoral components in early and mid flexion. Based on such analysis, it has been determined that paradoxical anterior translation of the femoral component relative to the tibial bearing may be reduced or otherwise delayed by increasing the radius of curvature of the condyle surface by an amount in the range of about 0.5 millimeters to about 5 millimeters or more at a degree of flexion in the range of about 30 degrees of flexion to about 90 degrees of flexion.

Figure 9:
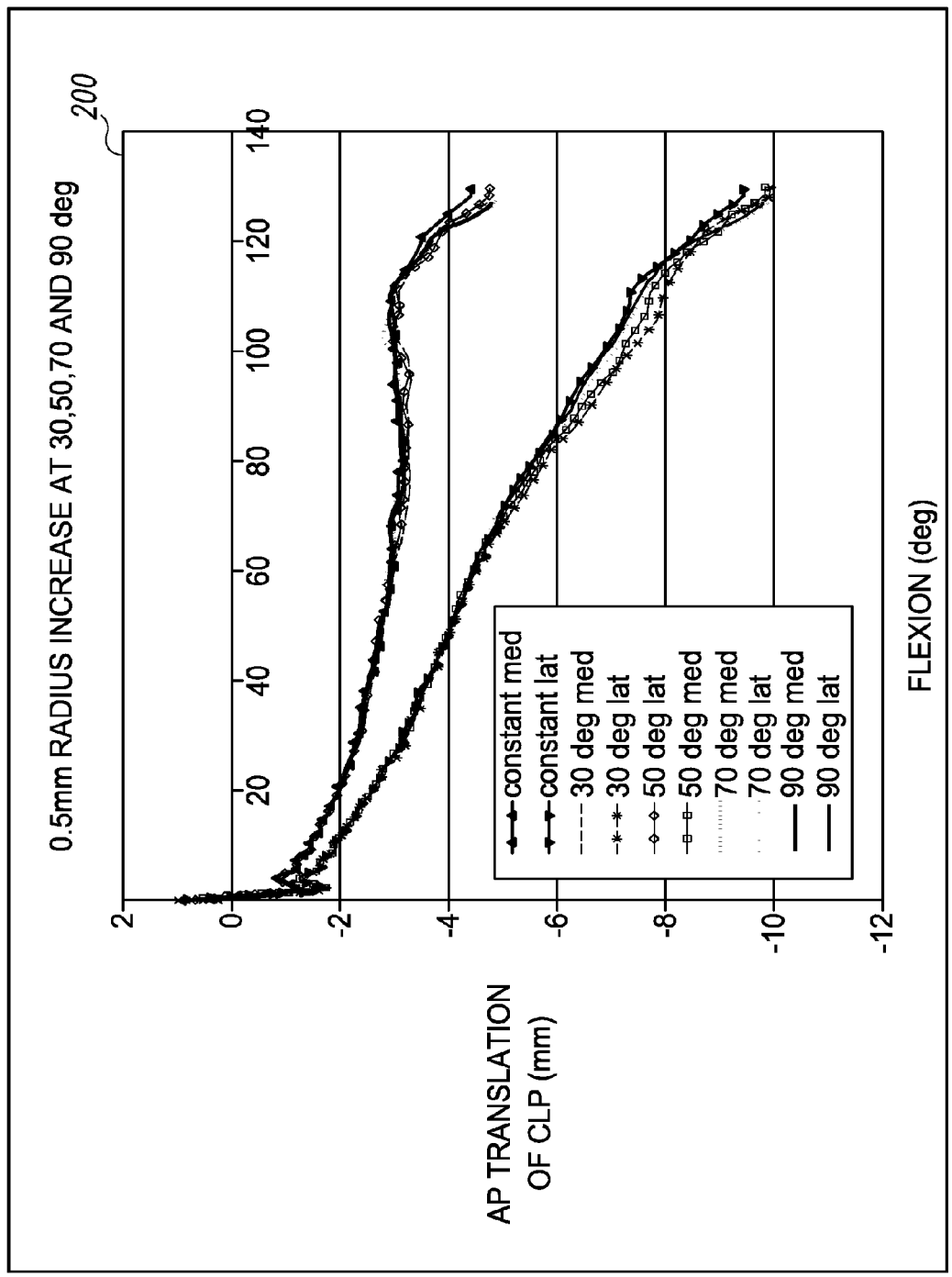
FIG. 9 is graph of the anterior-posterior translation of a simulated femoral component having an increased radius of curvature located at various degrees of flexion.
Figure 10:
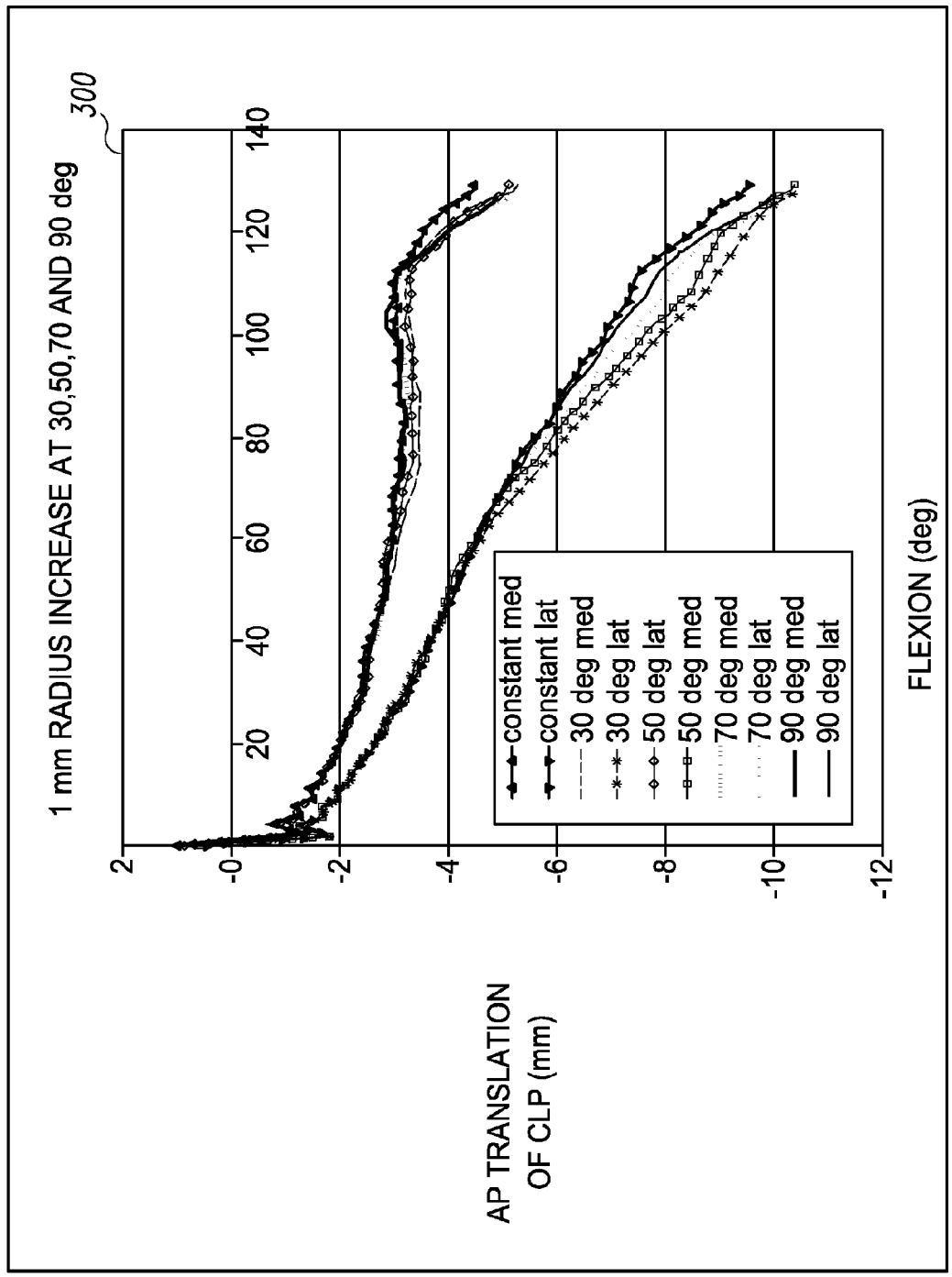
FIG. 10 is graph of the anterior-posterior translation of another simulated femoral component having an increased radius of curvature located at various degrees of flexion.
Figure 11:
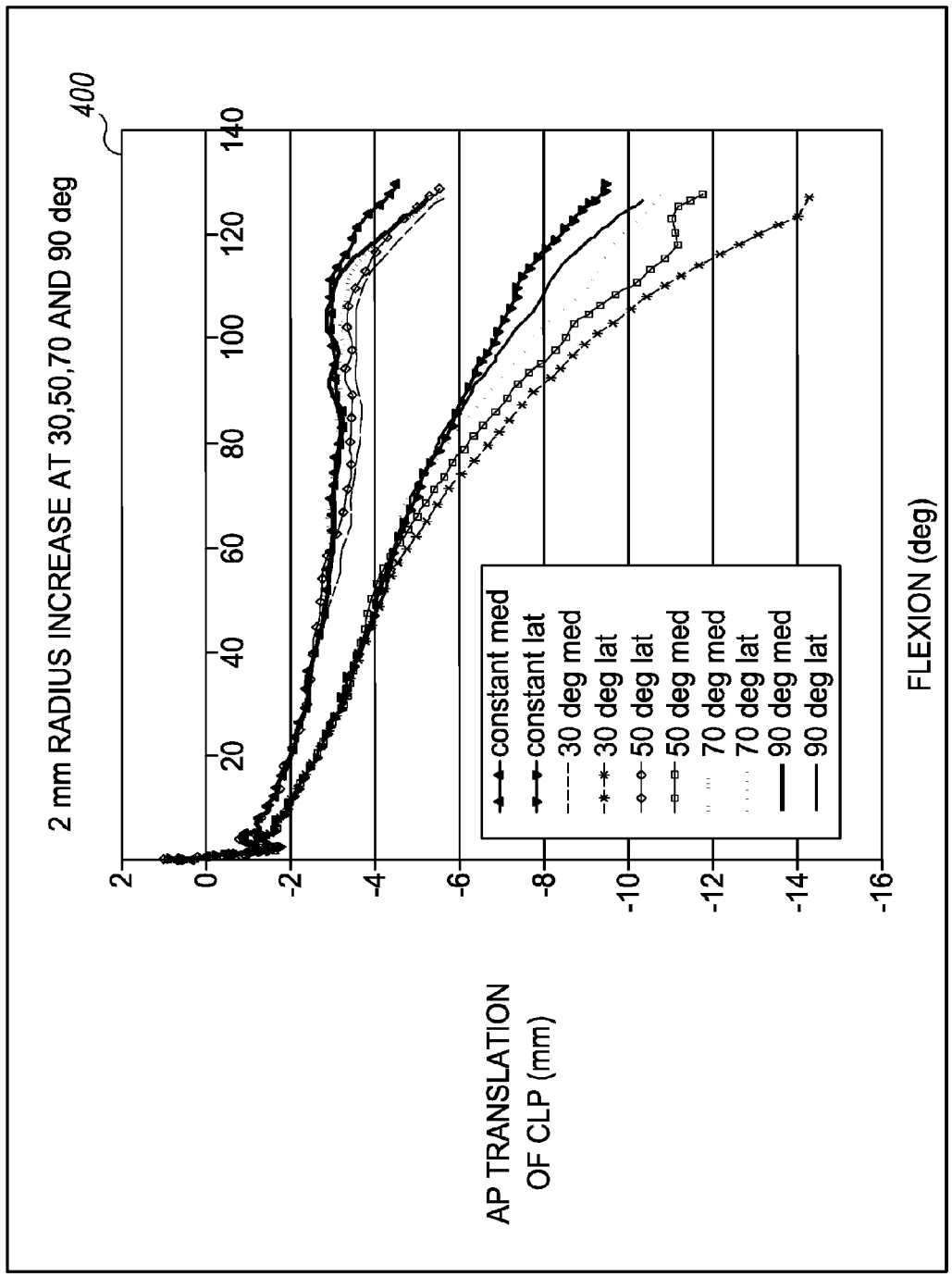
FIG. 11 is graph of the anterior-posterior translation of another simulated femoral component having an increased radius of curvature located at various degrees of flexion.
Figure 12:
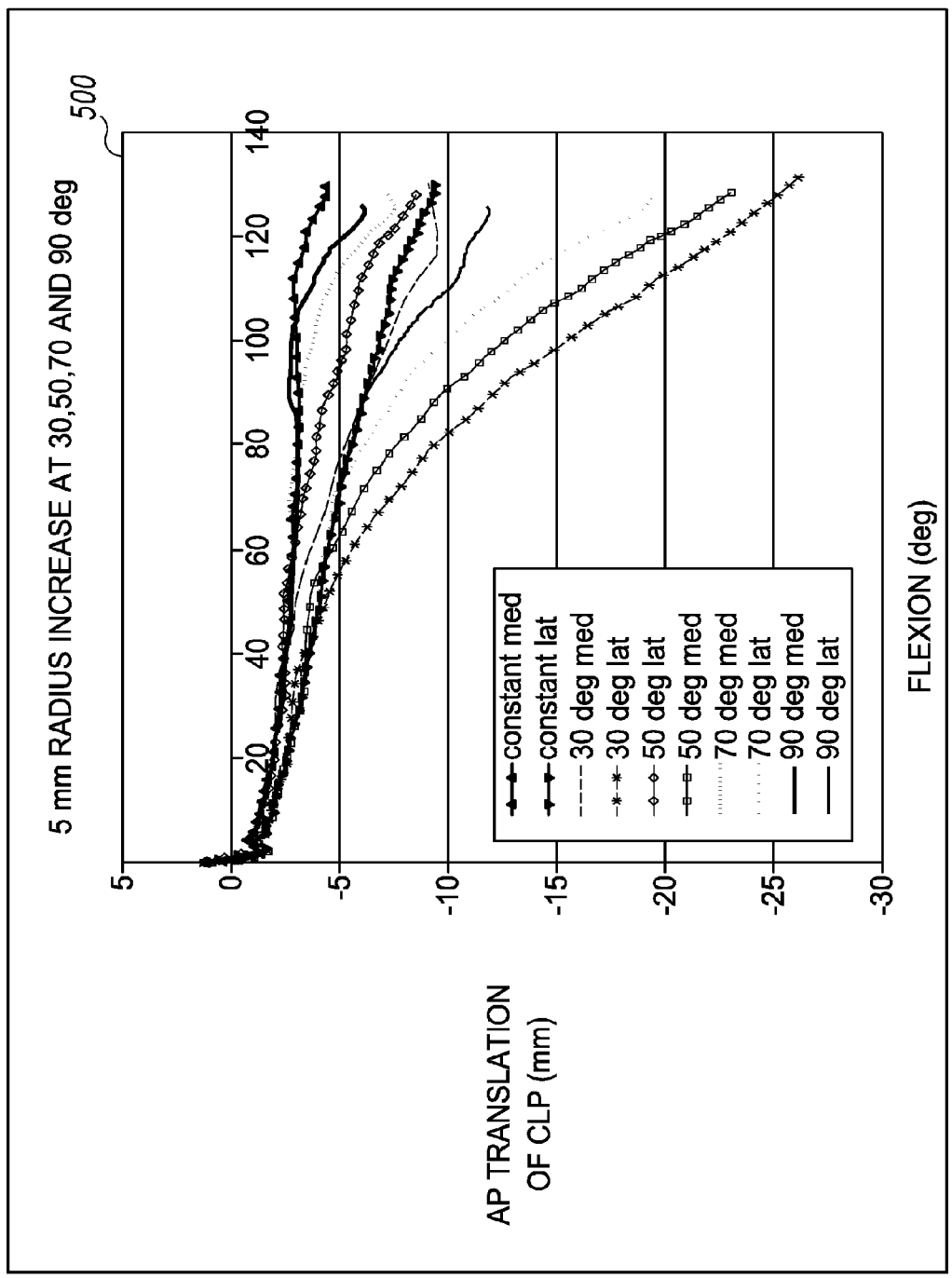
FIG. 12 is graph of the anterior-posterior translation of another simulated femoral component having an increased radius of curvature located at various degrees of flexion.

For example, the graph 200 illustrated in FIG. 9 presents the results of a deep bending knee simulation using a femoral component wherein the radius of curvature of the condyle surface is increased by 0.5 millimeters (i.e., from 25.0 millimeters to 25.5 millimeters) at 30 degrees of flexion, at 50 degrees of flexion, at 70 degrees of flexion, and at 90 degrees of flexion. Similarly, the graph 300 illustrated in FIG. 10 presents the results of a deep bending knee simulation using a femoral component wherein the radius of curvature of the condyle surface is increased by 1.0 millimeters (i.e., from 25.0 millimeters to 26.0 millimeters) at 30 degrees of flexion, at 50 degrees of flexion, at 70 degrees of flexion, and at 90 degrees of flexion. The graph 400 illustrated in FIG. 11 presents the results of a deep bending knee simulation using a femoral component wherein the radius of curvature of the condyle surface is increased by 2.0 millimeters (i.e., from 25.0 millimeters to 27.0 millimeters) at 30 degrees of flexion, at 50 degrees of flexion, at 70 degrees of flexion, and at 90 degrees of flexion. Additionally, the graph 500 illustrated in FIG. 12 presents the results of a deep bending knee simulation using a femoral component wherein the radius of curvature of the condyle surface is increased by 5.0 millimeters (i.e., from 25.0 millimeters to 26.0 millimeters) at 30 degrees of flexion, at 50 degrees of flexion, at 70 degrees of flexion, and at 90 degrees of flexion.

In the graphs 200, 300, 400, 500, the condylar lowest or most distal points (CLP) of the medial condyle ("med") and the lateral condyle ("lat") of the femoral component are graphed as a representation of the relative positioning of the femoral component to the tibial bearing. As such, a downwardly sloped line represents roll-back of the femoral component on the tibial bearing and an upwardly sloped line represents anterior translation of the femoral component on the tibial bearing.

As illustrated in the graphs 200, 300, 400, 500, anterior sliding of the femoral component was delayed until after about 100 degrees of flexion in each of the embodiments; and the amount of anterior translation was limited to less than about 1 millimeter. In particular, "roll-back" of the femoral component on the tibial bearing was promoted by larger increases in the radius of curvature of the condyle surface at earlier degrees of flexion. Of course, amount of increase in the radius of curvature and the degree of flexion at which such increase is introduced is limited by other factors such as the anatomical joint space of the patient's knee, the size of the tibial bearing, and the like. Regardless, based on the simulations reported in the graphs 200, 300, 400, 500, paradoxical anterior translation of the femoral component on the tibial bearing can be reduced or otherwise delayed by increasing the radius of curvature of the condyle surface of the femoral component during early to mid flexion.

Accordingly, referring back to FIGS. 5-8, the condyle surface 100 in the sagittal plane is formed in part from a number of curved surface sections 102, 104, 106, 108 the sagittal ends of each of which are tangent to the sagittal ends of any adjacent curved surface section of the condyles surface 100. Each curved surface section 102, 104, 106, 108 is defined by a radius of curvature. In particular, the curved surface section 102 is defined by a radius of curvature R2, the curved surface section 104 is defined by a radius of curvature R3, the curved surface section 106 is defined by a radius of curvature R4.

The condyle surface 100 of the femoral component 12 is configured such that the radius of curvature R3 of the curved surface section 104 is greater than the radius of curvature R2 of the curved surface section 102. In one embodiment, the radius of curvature R3 is greater than the radius of curvature R2 by 0.5 millimeters or more. In another embodiment, the radius of curvature R3 is greater than the radius of curvature R2 by 2 millimeters or more. In another embodiment, the radius of curvature R3 is greater than the radius of curvature R2 by 2 millimeters or more. In a particular embodiment, the radius of curvature R3 is greater than the radius of curvature R2 by at least 5 millimeters or more. It should be appreciated, however, that the particular increase of radius of curvature between R2 and R3 may be based on or scaled to the particular size of the femoral component 12 in some embodiments.

Each of the curved surface sections 102, 104, 106, 108 contacts be bearing surface 42 (or 44) of the tibial bearing 14 through different ranges of degrees of flexion. For example, the curved surface section 102 extends from an earlier degree of flexion θ1 to a later degree of flexion θ2. The curved surface section 104 extends from the degree of flexion θ2 to a later degree of flexion θ3. The curved surface section 106 extends from the degree of flexion θ3 to a later degree of flexion θ4.

Figure 5:
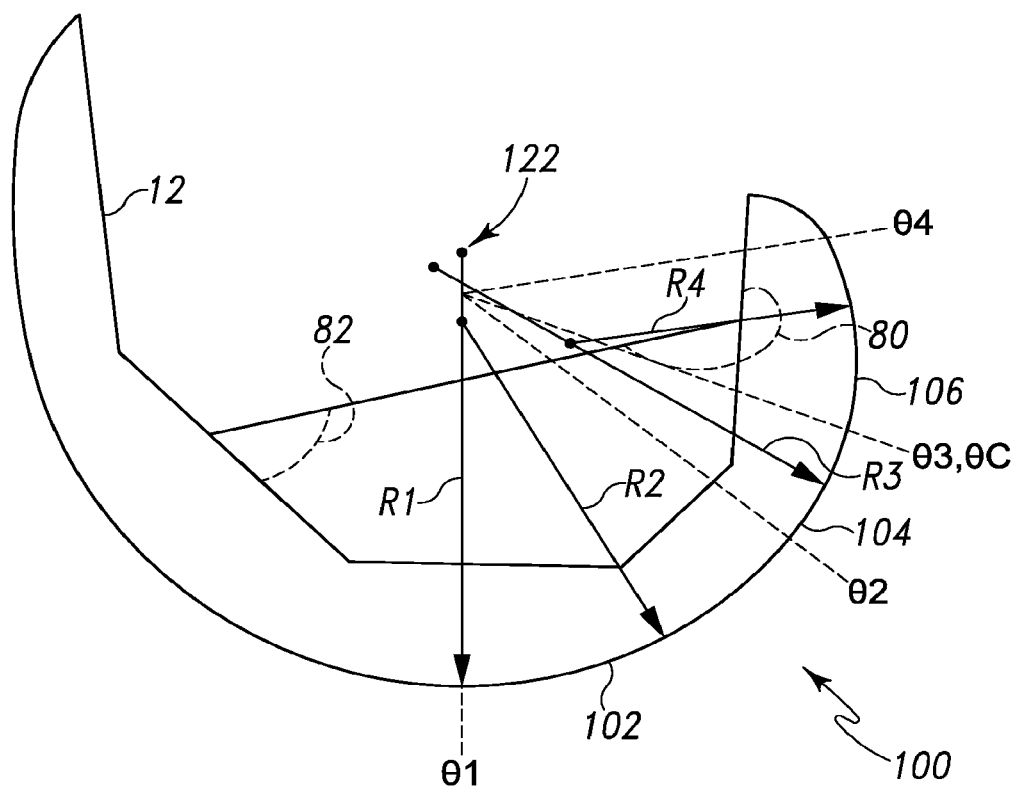
FIG. 5 is a cross-section view of one embodiment of the femoral component of FIG. 1.

For example, in one embodiment, as illustrated in FIG. 5, the curved surface section 102 extends from a degree of flexion θ1 of about 0 degrees of flexion to a degree of flexion θ2 of about 50 degrees of flexion. The curved surface section 104 extends from the degree of flexion θ2 of about 50 degrees of flexion to a degree of flexion θ3 of about 70 degrees of flexion. The curved surface section 106 extends from the degree of flexion θ3 of about 70 degrees of flexion to a degree of flexion θ4 of about 120 degrees of flexion. In the illustrative embodiment of FIG. 5, the posterior cam 80 of the femoral component 12 is configured to engage or contact the spine 60 of the tibial bearing 14 at a degree of flexion θC of about 70 degrees of flexion. However, in other embodiments, the posterior cam 80 may be configured to engage the spine 60 at a degree of flexion earlier or later than 70 degrees. By ensuring the posterior cam 80 engages or contacts the spine 60 prior to or soon after the reduction in radius of curvature from R3 to R4, the control of the kinematics of the orthopaedic prosthesis can be transitioned from the geometry of the condyle surface 100 to the interaction of the posterior cam 80 and spine 60, which may further reduce the amount of anterior translation of the femoral component 12. For example, in one particular embodiment, the posterior cam 80 may be configured to engage or contact the spine 60 at a degree of flexion θC that is no greater than 10 degrees more than the degree of flexion θ3 at which the radius curvature of the condyle surface 100 decreases from the radius of curvature R3 to the radius of curvature R4.

Figure 6:
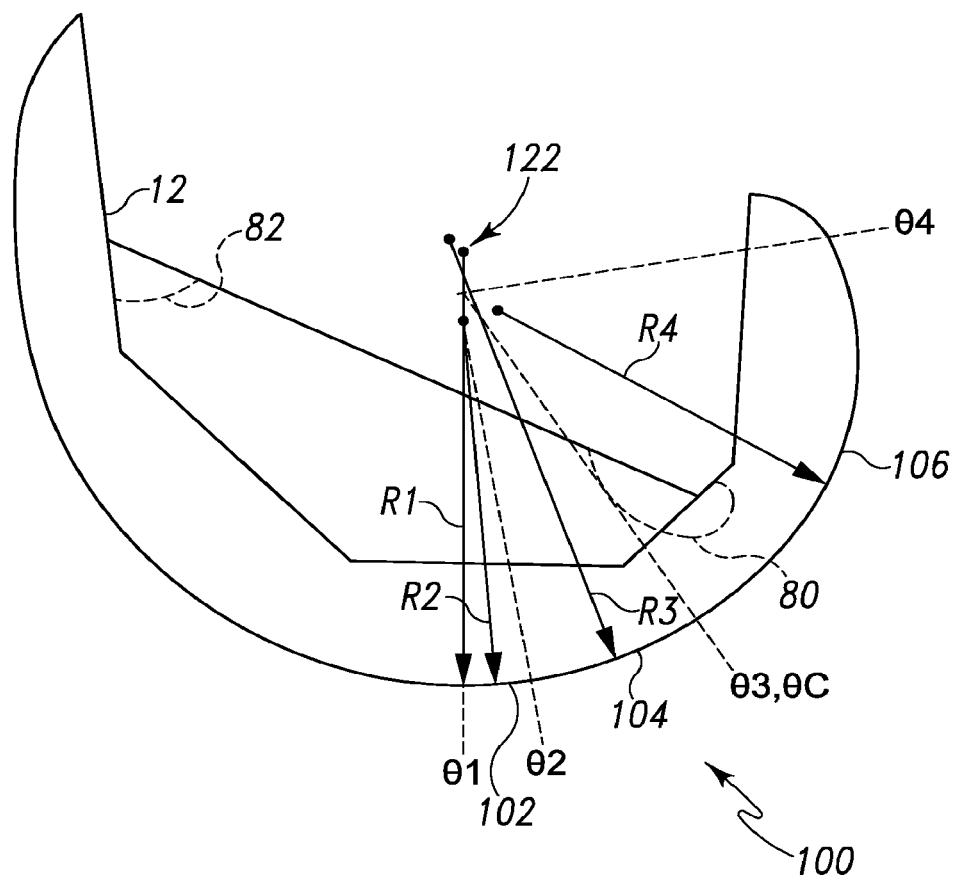
FIG. 6 is a cross-section view of another embodiment of the femoral component of FIG. 1.

In another embodiment, as illustrated in FIG. 6, the curved surface section 102 extends from a degree of flexion θ1 of about 0 degrees of flexion to a degree of flexion θ2 of about 10 degrees of flexion. The curved surface section 104 extends from the degree of flexion θ2 of about 10 degrees of flexion to a degree of flexion θ3 of about 30 degrees of flexion. The curved surface section 106 extends from the degree of flexion θ3 of about 30 degrees of flexion to a degree of flexion θ4 of about 120 degrees of flexion. In the illustrative embodiment of FIG. 6, the posterior cam 80 of the femoral component 12 is configured to engage or contact the spine 60 of the tibial bearing 14 at a degree of flexion θC of about 30 degrees of flexion. Again, however, the posterior cam 80 may be configured to engage the spine 60 at a degree of flexion earlier than 30 degrees (i.e., earlier than the reduction in radius of curvature from R3 to R4) or soon thereafter (e.g., within 0-10 degrees) in other embodiments.

Figure 7:
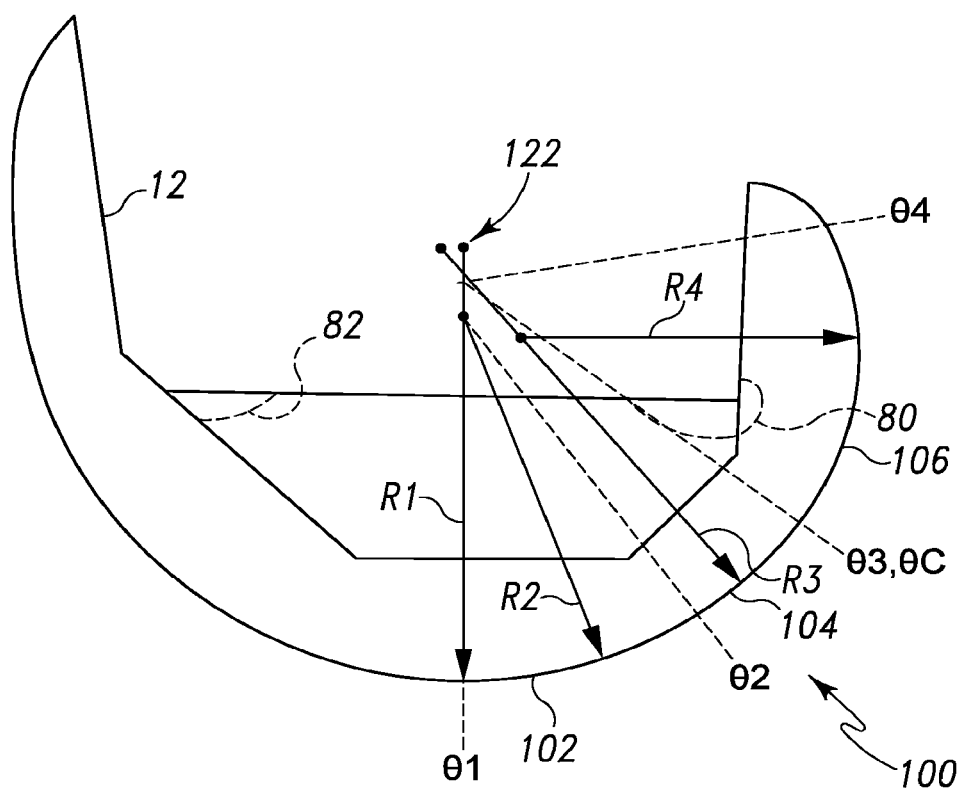
FIG. 7 is a cross-section view of another embodiment of the femoral component of FIG. 1.

In another embodiment, as illustrated in FIG. 7, the curved surface section 102 extends from a degree of flexion θ1 of about 0 degrees of flexion to a degree of flexion θ2 of about 30 degrees of flexion. The curved surface section 104 extends from the degree of flexion θ2 of about 30 degrees of flexion to a degree of flexion θ3 of about 50 degrees of flexion. The curved surface section 106 extends from the degree of flexion θ3 of about 50 degrees of flexion to a degree of flexion θ4 of about 120 degrees of flexion. In the illustrative embodiment of FIG. 7, the posterior cam 80 of the femoral component 12 is configured to engage or contact the spine 60 of the tibial bearing 14 at a degree of flexion θC of about 50 degrees of flexion. Again, however, the posterior cam 80 may be configured to engage the spine 60 at a degree of flexion earlier than 50 degrees (i.e., earlier than the reduction in radius of curvature from R3 to R4) or soon thereafter (e.g., within 0-10 degrees) in other embodiments.

Figure 8:
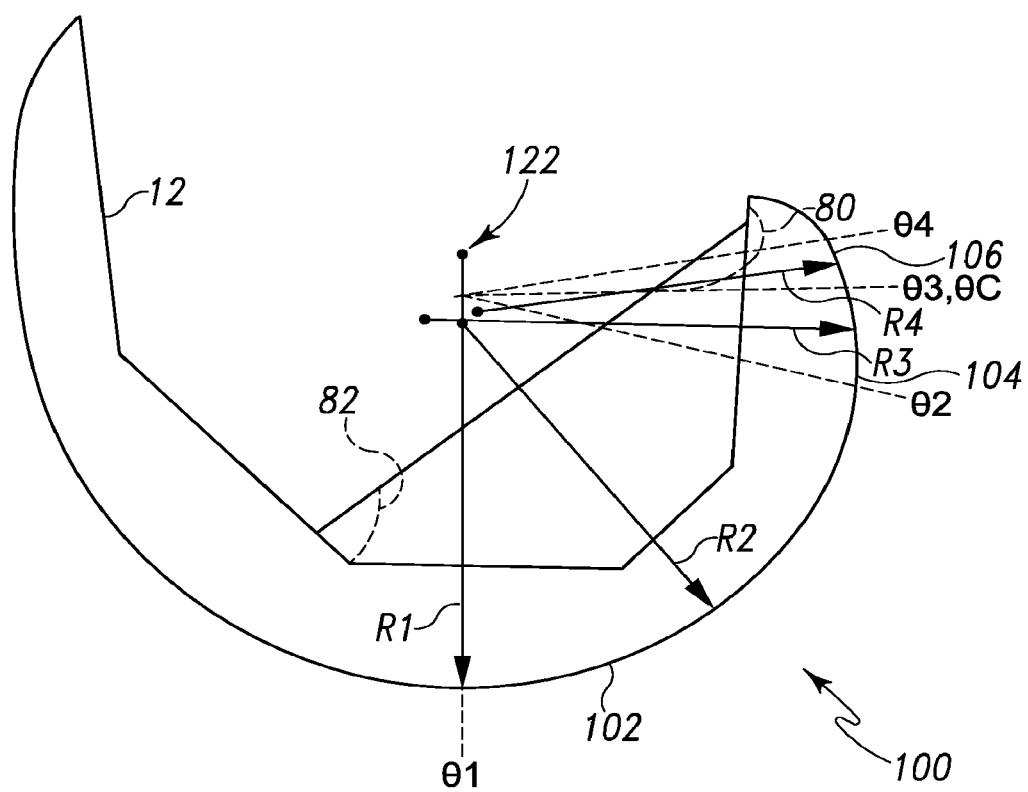
FIG. 8 is a cross-section view of another embodiment of the femoral component of FIG. 1.

In another embodiment, as illustrated in FIG. 8, the curved surface section 102 extends from a degree of flexion θ1 of about 0 degrees of flexion to a degree of flexion θ2 of about 70 degrees of flexion. The curved surface section 104 extends from the degree of flexion θ2 of about 70 degrees of flexion to a degree of flexion θ3 of about 90 degrees of flexion. The curved surface section 106 extends from the degree of flexion θ3 of about 90 degrees of flexion to a degree of flexion θ4 of about 120 degrees of flexion. In the illustrative embodiment of FIG. 8, the posterior cam 80 of the femoral component 12 is configured to engage or contact the spine 60 of the tibial bearing 14 at a degree of flexion θC of about 90 degrees of flexion. Again, however, the posterior cam 80 may be configured to engage the spine 60 at a degree of flexion earlier than 90 degrees (i.e., earlier than the reduction in radius of curvature from R3 to R4) or soon thereafter (e.g., within 0-10 degrees) in other embodiments.

It should be appreciated that the embodiments of FIGS. 5-8 are illustrative embodiments and, in other embodiments, each of the curved surface sections 102, 104, 106 may extend from degrees of flexion different from those shown and discussed above in regard to FIGS. 5-8. For example, in each of the embodiments of FIGS. 5-8, although the curved surface section 102 is illustrated as beginning at about 0 degrees of flexion, the curved surface section 102 may being at a degree of flexion prior to 0 degrees of flexion (i.e., a degree of hyperextension) in other embodiments.

Additionally, it should be appreciated that the degree of flexion θC at which the posterior cam 80 contacts the spine 60 may be less than, substantially equal to, or slightly greater than the degree of flexion θ3 at which the radius of curvature R3 decreases to the radius of curvature R4. In some embodiments, the degree of flexion θC is within a predetermined threshold of the degree of flexion θ3. For example, in one particular embodiment, the degree of flexion θC is within about 10 degrees of the degree of flexion θ3. For example, the radius of curvature R3 may decrease to the radius of curvature R4 at a degree of flexion θ3 of about 70 degrees and the posterior cam 80 may be configured to initially contact the spine 60 at a degree of flexion θC of in the range of about 60 to about 80 degrees of flexion.

Figure 13:
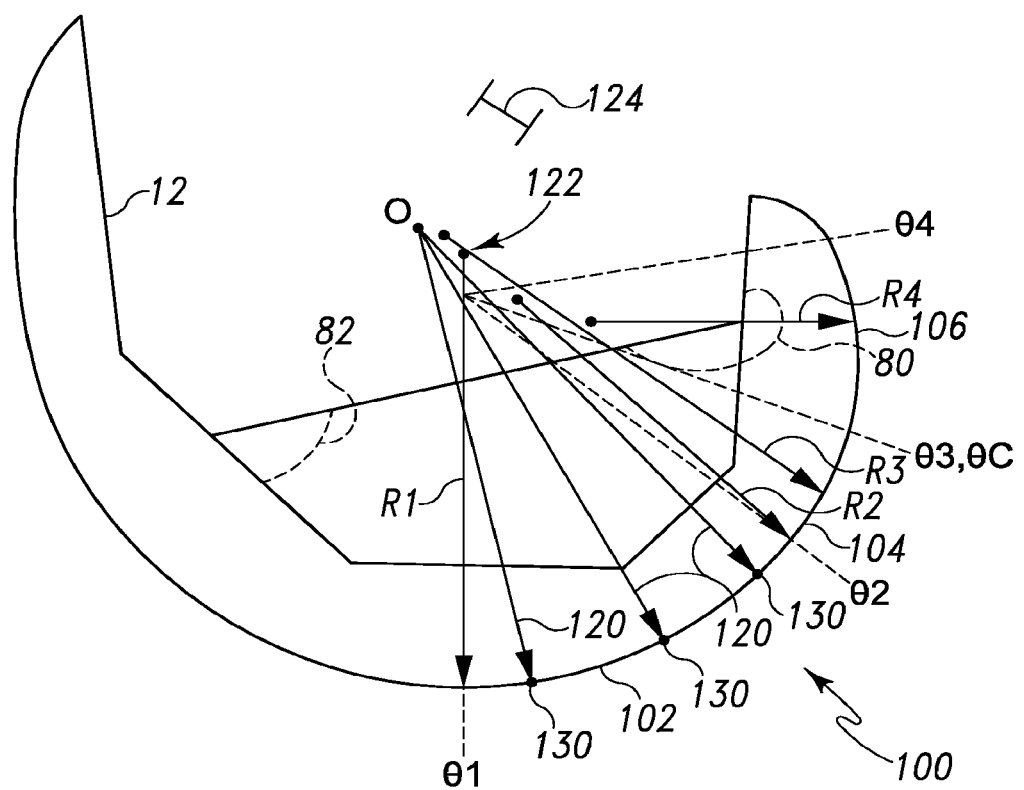
FIG. 13 is a cross-sectional view of another embodiment of the femoral component of FIG. 1.
Figure 15:
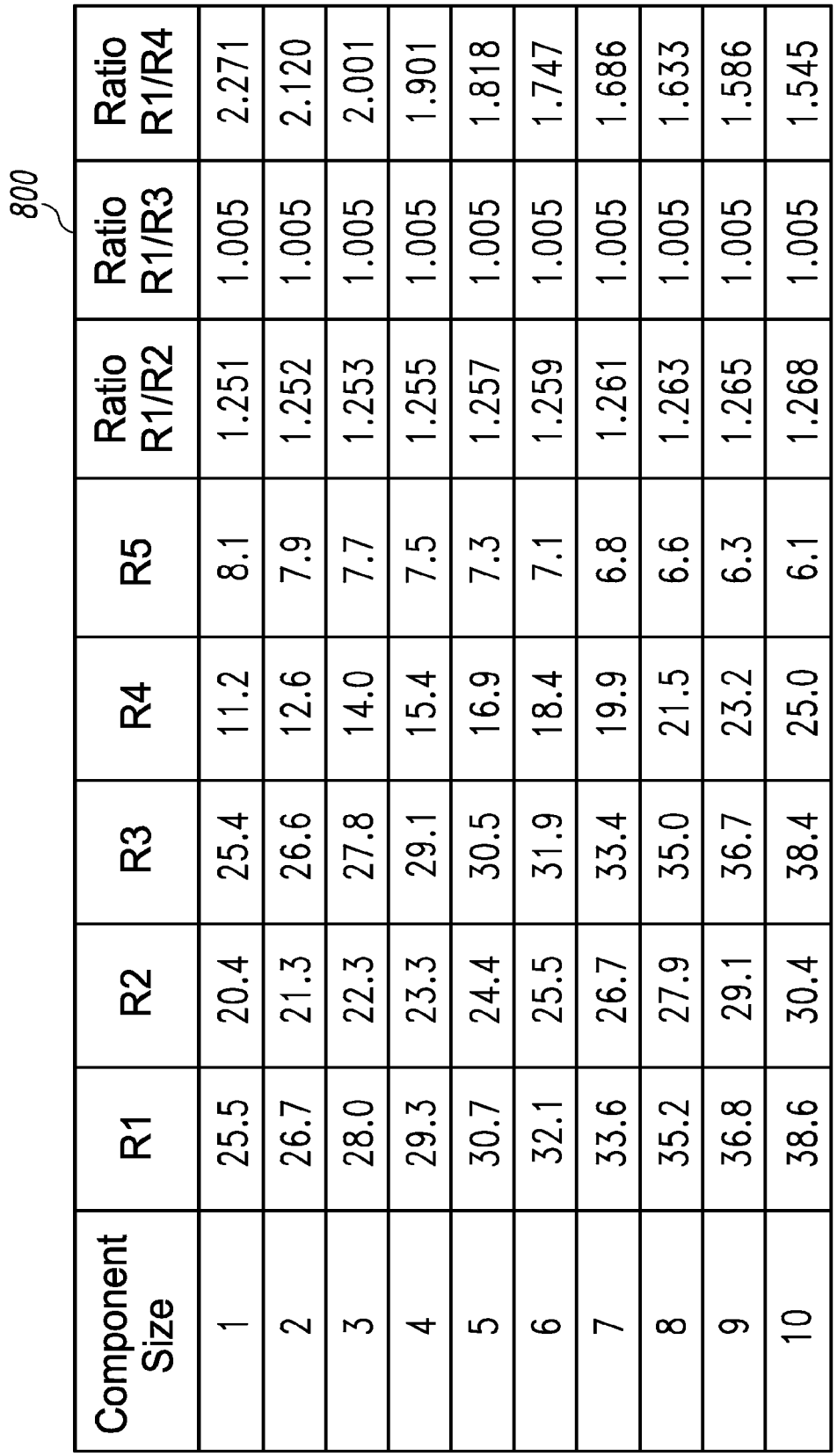
FIG. 15 is a table of one embodiment of radii of curvature values and ratios for a family of femoral component sizes.

Referring now to FIGS. 13-15, in some embodiments, the condyle surface 100 includes a gradual transition between discreet radii of curvature in the early to mid flexion ranges such that the change in the radius of curvature of the condyle surface over a range of degrees of flexion is reduced. For example, as illustrated in FIG. 13, the curved surface section 102 in some embodiments is designed to provide a gradual transition from the first radius of curvature R1 to the second radius of curvature R2. To do so, the curved surface section 102 is defined by a plurality of rays 120 rather than a constant radius of curvature as illustrated in and described above in regard to FIGS. 5-8. Each of the plurality of rays 120 originate from a common origin O. Additionally, each of the plurality of rays 120 defines a respective contact point 130 on the curved surface section 120. Although only three rays 120 are illustrated in FIG. 13 for clarity of the drawing, it should be appreciated that an infinite number of rays 120 may be used to define the curved surface section 102.

The location of each contact points 130, which collectively define the curved surface section 102, can be determined based on the length of each ray 120 at each degree of flexion. In particular and unexpectedly, it has been determined that paradoxical anterior translation of the femoral component 12 on the tibial bearing 14 may be reduced or delayed by defining the curved surface section 102 according to the following polynomial equation:

$$r_\theta = (a + (b*\theta) + (c*\theta^2) + (d*\theta^3)), \quad (3)$$

wherein "$r_\theta$" is the length of a ray 120 (in metric units) defining a contact point 130 on the curved surface section 104 at "θ" degrees of flexion, "a" is a scalar value between 20 and 50, and "b" is a coefficient value selected such that:

$$-0.30 < b < 0.00,$$

$$0.00 < b < 0.30, \text{ or}$$

$$b = 0 \quad (4)$$

If the selected coefficient "b" is in the range of −0.30<b<0.00, then coefficients "c" and "d" are selected such that:

$$0.00 < c < 0.012, \text{ and}$$

$$-0.00015 < d < 0.00. \quad (5)$$

Alternatively, if the selected coefficient "b" is in the range of 0.00<b<0.30, then coefficients "c" and "d" are selected such that:

$$-0.010 < c < 0.00, \text{ and}$$

$$-0.00015 < d < 0.00. \quad (6)$$

Further, if the selected coefficient "b" is equal to 0, then coefficients "c" and "d" are selected such that:

$$-0.0020 < c < 0.00, \text{ or}$$

$$0.00 < c < 0.0025, \text{ and}$$

$$-0.00015 < d < 0.00. \quad (7)$$

It should be appreciated that ranges of values for the scalar "a" and coefficients "b", "c", and "d" have been determined from an infinite number of possible solutions for the polynomial equation (3). That is, the particular set of ranges provided above have been determined to generate a family of curves (i.e., the curved surface section 102) that provide a gradual transitioning of the condyle surface 100 from the radius of curvature R1 to the radius of curvature R2 such that anterior translation of the femoral component 12 relative to the tibial bearing 14 is reduced or delayed. Additionally, it should be appreciated that the range of values for each coefficient "a", "b", "c", and "d" are provided above in regard to embodiments designed using the metric system of units. However, such range of coefficient values may be converted for use in embodiments using other systems of units such as the English system of units.

The overall shape of the curved surface section 102 is also affected by the placement of the common origin O of the plurality of rays 120. By limiting the distance 124 between the common origin O of the plurality of rays 120 and the origin 122 of the distal radius of curvature R1, paradoxical anterior sliding of the femoral component 12 on the tibial bearing 14 may be reduced or delayed. Additionally, stability of the orthopaedic knee prosthesis 10 may be improved by ensuring the common origin O of the plurality of rays 120 is within the predetermined distance 124 from the origin 122 of the distal radius of curvature R1. As such, in one embodiment, the location of the common origin O of the plurality of rays 120 is selected such that the distance 124 between the common origin O and the origin 120 of the radius of curvature R1 is less than about 10 millimeters to reduce or delay anterior translation of the femoral component and/or provide improved stability to the orthopaedic knee prosthesis 10.

It should be appreciated that the distance 124 between the common origin O and the origin 122 of the radius of curvature R1 and the particular coefficient values may be dependent upon the particular size of the femoral component 12 in some embodiments. For example, as illustrated in FIG. 14, a table 700 illustrates one particular embodiment of coefficient values for the above-defined polynomial equation (3) and values for the distance 124 defined between the common origin O and the origin 122 of the distal radius of curvature R1. As shown in table 700, the distance 124 between the common origin O and the origin 122 of the radius of curvature R1 and the value for the scalar "a" change across the femoral component sizes. However, in this particular embodiment, the values for the coefficients "b", "c", and "d" are constant across the femoral component sizes. It should be appreciated, however, that in other embodiments, the coefficient values "b", "c", and "d" may change across the femoral component sizes.

As discussed above, in some embodiments, the condyle surface 100 is further designed or configured such that the change in the radius of curvature of the condyle surface 100 in the early and mid flexion ranges is not too great or too abrupt (e.g., the ratio of the degree of change in radius of curvature to the change in degrees of flexion is too great). That is, if the ratio of the radius of curvature R1 to the radius of curvature R2, R3, or R4 is too great, paradoxical anterior translation of the femoral component 12 may occur. As such, by designing the condyle surface 100 of the femoral component 12 such that the ratios of the distal radius of curvature R1 to (i) the radius of curvature R2 of the curved surface section 102, (ii) the radius of curvature R3 of the curved surface section 104, and (iii) the radius of curvature R4 of the late flexion curved surface section 106 are less than a predetermined threshold value, paradoxical anterior sliding may unexpectedly be reduced or otherwise delayed.

Accordingly, in one particular embodiment, the condyle surface 100 of the femoral component 12 is designed such that the ratio of the radius of curvature of R1 to the radius of curvature of R2 is between about 1.10 to about 1.30, the ratio of the radius of curvature of R1 to the radius of curvature R3 is between about 1.001 to about 1.100, and the ratio of the radius of curvature of R1 to the radius of curvature R4 is about 1.25 to about 2.50. Further, in some embodiments, the ratio of the radius of curvature of R2 to the radius of curvature of R3 is between about 0.74 and about 0.85.

It should be appreciated that the particular amount of increase in the radius of curvature R2 to R3 of the condyle surface 100 of the femoral component 12 and/or the positioning of such increase on the condyle surface 100 may also be based on, scaled, or otherwise affected by the size of the femoral component 12. That is, it should be appreciated that an increase of the radius of curvature R2 to R3 of the condyle surface 100 of 0.5 millimeters is a relatively larger increase in small-sized femoral components compared to larger-sized femoral components. As such, the magnitude of the increase in the radius of curvature R2 to R3 of the condyle surface 100 of the femoral component 12 may change across femoral component sizes. In one embodiment, however, the ratios of the radius of curvatures R1 to the radius of curvatures R2, R3, and R4 are maintained at a substantially constant value across the family of femoral component sizes.

For example, as illustrated in FIG. 15, a table 800 defines the length of each radius of curvature R1, R2, R3, R4 for a family of femoral component sizes 1 through 10. As illustrated in the table 850, the length of each radius of curvature R1, R2, R3, R4 for each size 1-10 of the femoral component 12 is selected such that the ratios of R1/R2 and R1/R3 are substantially constant across the femoral component sizes. In the illustrative embodiment, as previously discussed, the ratio of the radius of curvature R1 to the radius of curvature R2 is maintained at a value of about 1.25 to about 1.27 across the femoral component sizes 1 through 10 and the ratio of the radius of curvature R1 to the radius of curvature R3 is maintained at a value of about 1.005 across the femoral component sizes 1 through 10.

Figure 16:
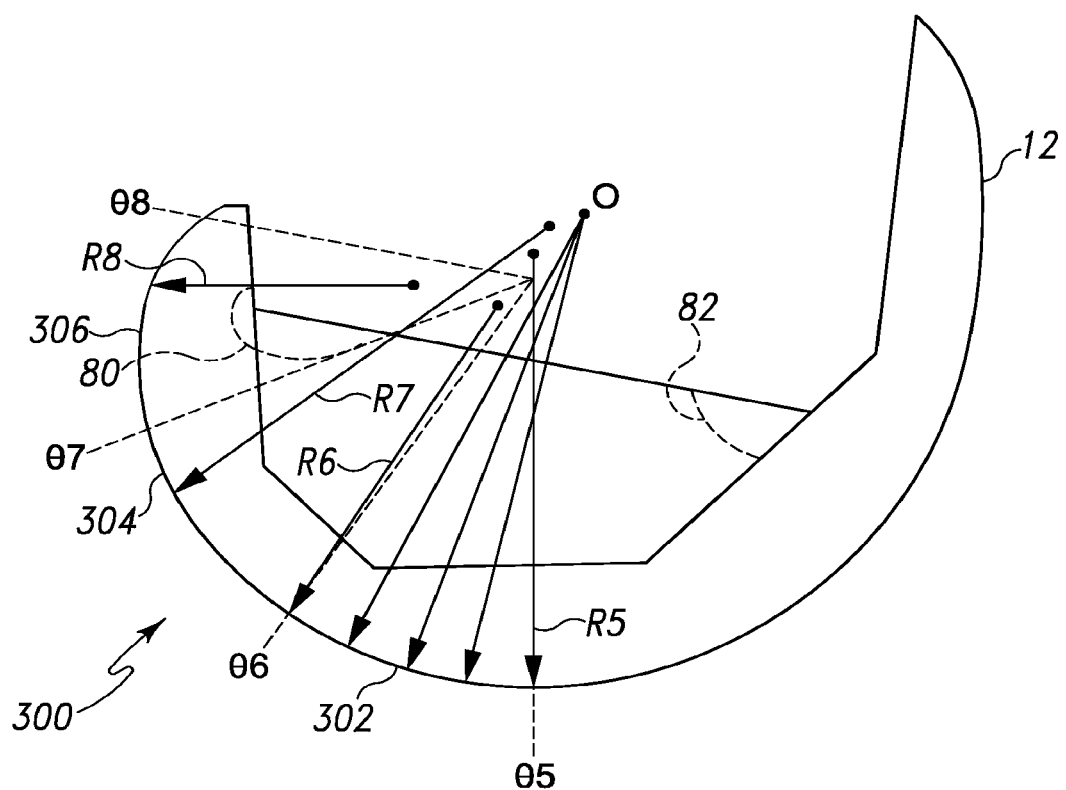
FIG. 16 is a cross-section view of another condyle of another embodiment of the femoral component of FIG. 1.

The overall shape and design of the condyle surface 100 of the femoral component 12 has been described above in regard to a single condyle 52, 54 of the femoral component 12. It should be appreciated that in some embodiments both condyles 52, 54 of the femoral component 12 may be symmetrical and have similar condyle surfaces 100. However, in other embodiments, the condyles 52, 54 of the femoral component 12 may be asymmetrical. For example, as illustrated in FIG. 16, the femoral component 12 may include a second condyle 52, 54 having a condyle surface 300, which is defined in part by a plurality of curved surface sections 302, 304, 306. The curved surface section 302 extends from an earlier degree of flexion θ5 to a later degree of flexion θ6. The curved surface section 304 extends from the degree of flexion θ6 to a later degree of flexion θ7. The curved surface section 306 extends from the degree of flexion θ7 to a later degree of flexion θ8. The condyle surface 300 also includes a distal radius R5, which is gradually transitioned to a radius of curvature R6 via the curved surface section 302. Additionally, the curved section 304 is defined by a radius of curvature R7 and the curved section 306 is defined by a radius of curvature R8.

As such, in embodiments wherein the condyles 52, 54 are symmetrical, the degree of flexion θ5 is substantially equal to the degree of flexion θ1, the degree of flexion θ6 is substantially equal to the degree of flexion θ2, the degree of flexion θ7 is substantially equal to the degree of flexion θ3, and the degree of flexion θ8 is substantially equal to the degree of flexion θ4. Additionally, the radius of curvature R5 is substantially equal to the radius of curvature R1, the radius of curvature R6 is substantially equal to the radius of curvature R2, the radius of curvature R7 is substantially equal to the radius of curvature R3, and the radius of curvature R8 is substantially equal to the radius of curvature R4. Further, the set of coefficient values "a", b", "c", and/or "d" of the equation (4) described above are substantially similar for both condyles.

However, in other embodiments, the condyles 52, 54 are asymmetrical. As such, the degree of flexion θ5 may be different from the degree of flexion θ1. Additionally, the degree of flexion θ6 may be different from the degree of flexion θ2. That is, the increase in radius of curvature between R2 and R3 may occur at different degrees of flexion between the condyles 52, 54. Further, the degree of flexion θ8 may be different from the degree of flexion θ4. It should be appreciated, however, that the degree of flexion θ7 may be substantially equal to the degree of flexion θ3 such that the posterior cam 80 is positioned properly within the intracondylar notch 56.

Additionally, in those embodiments wherein the condyles 52, 54 are asymmetrical, the radius of curvature R5 may be different from the radius of curvature R1, the radius of curvature R6 may be different from the radius of curvature R2, the radius of curvature R7 may be different from the radius of curvature R3, and/or the radius of curvature R8 may be different from the radius of curvature R4. Further, the set of coefficient values "a", b", "c", and/or "d" of the equation (3) described above may be different between the condyle surfaces 100 and 300.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the devices and assemblies described herein. It will be noted that alternative embodiments of the devices and assemblies of the present disclosure may not include all of the features described yet still benefit from at least some of the advantages of such features. Those of ordinary skill in the art may readily devise their own implementations of the devices and assemblies that incorporate one or more of the features of the present invention and fall within the spirit and scope of the present disclosure as defined by the appended claims.

The invention claimed is:

1. A posterior stabilized orthopaedic knee prosthesis comprising:
a femoral component including (i) a pair of spaced apart condyles defining an intracondylar notch therebetween, at least one of the pair of spaced apart condyles having a condyle surface curved in the sagittal plane and (ii) a posterior cam positioned in the intracondylar notch; and
a tibial bearing including (i) a platform having a bearing surface configured to articulate with the condyle surface of the femoral component and (ii) a spine extending upwardly from the platform,
wherein the condyle surface of the femoral component (i) contacts the bearing surface at a first contact point on the condyle surface at a first degree of flexion, the first degree of flexion being less than about 30 degrees, (ii) contacts the bearing surface at a second contact point on the condyle surface at a second degree of flexion, the second degree of flexion being in the range of 35 degrees to 90 degrees, (iii) contacts the bearing surface at a third contact point on the condyle surface at a third degree of flexion, the third degree of flexion being greater than the second degree of flexion, and (iv) contacts the bearing surface at a plurality of contact points between the first contact point and the second contact point when the femoral component is moved from the first degree of flexion to the second degree of flexion,
wherein the posterior cam of the femoral component contacts the spine of the tibial bearing at a fourth degree of flexion, the fourth degree of flexion being no greater than about 10 degrees more than the third degree of flexion,
wherein each contact point of the plurality of contact points is defined by a ray extending from a common origin to the respective contact point of the plurality of contact points, each ray having a length defined by the following polynomial equation:

$$r_\theta = (a + (b*\theta) + (c*\theta^2) + (d*\theta^3)),$$

wherein $r_\theta$ is the length of the ray defining a contact point at θ degrees of flexion, a is a coefficient value between 20 and 50, and b is a coefficient value in a range of 0.00<b<0.30,
wherein (i) c is a coefficient value between −0.010 and 0.00 and (ii) d is a coefficient value between −0.00015 and 0.00,
wherein the condyle surface in the sagittal plane has a first radius of curvature at the first contact point and a second radius of curvature at the second contact point, the second radius of curvature being less than the first radius of curvature.

2. The posterior stabilized orthopaedic knee prosthesis of claim 1, wherein:
the first radius of curvature has an origin, and
the distance between the origin of the first radius of curvature and the common origin of the rays is in the range of 0 and 10 millimeters.

3. The posterior stabilized orthopaedic knee prosthesis of claim 1, wherein the first degree of flexion is in the range of 0 degrees to 10 degrees, the second degree of flexion is in the range of 45 degrees to 55 degrees, and the third degree of flexion is in the range of about 65 degrees to about 75 degrees.

4. The posterior stabilized orthopaedic knee prosthesis of claim 3, wherein the first degree of flexion is about 0 degrees, the second degree of flexion is about 50 degrees, and the third degree of flexion is about 70 degrees.

5. The posterior stabilized orthopaedic knee prosthesis of claim 1, wherein:
the condyle surface in the sagittal plane has a third radius of curvature at the third contact point, and
the condyle surface contacts the bearing surface at a fourth contact point on the condyle surface at the fourth degree of flexion, and the condyle surface has a fourth radius of curvature at the fourth contact point that is less than the second radius of curvature.

6. The posterior stabilized orthopaedic knee prosthesis of claim 5, wherein the third radius of curvature is less than the first radius of curvature.

7. The posterior stabilized orthopaedic knee prosthesis of claim 1, wherein the fourth degree of flexion is in a range of 70 degrees to 80 degrees.

8. The posterior stabilized orthopaedic knee prosthesis of claim 1, wherein:
the condyle surface is a first condyle surface of a first condyle of the pair of spaced apart condyles, and
the pair of spaced apart condyles includes a second condyle that includes a second condyle surface that is curved in the sagittal plane.

9. The posterior stabilized orthopaedic knee prosthesis of claim 8, wherein the first condyle surface and the second condyle surface are symmetrical.

10. The posterior stabilized orthopaedic knee prosthesis of claim 8, wherein the first condyle surface and the second condyle surface are asymmetrical.

11. A posterior stabilized orthopaedic knee prosthesis comprising:
a femoral component including (i) a pair of spaced apart condyles defining an
intracondylar notch therebetween, at least one of the pair of spaced apart condyles having a condyle surface curved in the sagittal plane and (ii) a posterior cam positioned in the intracondylar notch; and
a tibial bearing including (i) a platform having a bearing surface configured to articulate with the condyle surface of the femoral component and (ii) a spine extending upwardly from the platform,
wherein the condyle surface of the femoral component (i) contacts the bearing surface at a first contact point on the condyle surface at a first degree of flexion of about 0 degrees, (ii) contacts the bearing surface at a second contact point on the condyle surface at a second degree of flexion, the second degree of flexion being greater than the first degree of flexion and in the range of about 30 degrees to about 50 degrees, (iii) contacts the bearing surface at a third contact point on the condyle surface at a third degree of flexion, the third degree of flexion being greater than the second degree of flexion and in the range of about 70 degrees to about 120 degrees, and (iv) contacts the bearing surface at a fourth contact point on the condyle surface at a fourth degree of flexion, the fourth degree of flexion being greater than the third degree of flexion, wherein the condyle surface in the sagittal plane has a first radius of curvature at the first contact point, a second radius of curvature that is constant between the second contact point and the third contact point, and a third radius of curvature that is constant between the third contact point and the fourth contact point, the first radius of curvature being different from the second radius of curvature and the third radius of curvature, wherein the posterior cam of the femoral component includes an anterior surface configured to initially contact the spine of the tibial bearing at a fourth degree of flexion, the fourth degree of flexion being at least 70 degrees, and wherein the condyle surface has a plurality of radii of curvature between the first contact point and the second contact point to transition from the first radius of curvature to the second radius of curvature over a range of degrees of flexion, each of the plurality of radii of curvature originating from a common origin.

12. The posterior stabilized orthopaedic knee prosthesis of claim 11, wherein the second degree of flexion is no greater than about 30 degrees.

13. The posterior stabilized orthopaedic knee prosthesis of claim 11, wherein the range of degrees of flexion is about 50 degrees.

14. The posterior stabilized orthopaedic knee prosthesis of claim 11, wherein the condyle surface contacts the bearing surface at a plurality of contact points between the first contact point and the second contact point when the femoral component is moved from the first degree of flexion to the second degree of flexion, and each contact point of the plurality of contact points is defined by a ray extending from a common origin to the respective contact point of the plurality of contact points, each ray having a length defined by the following polynomial equation:

$$r_\theta = (a + (b*\theta) + (c*\theta^2) + (d*\theta^3)),$$

wherein $r_\theta$ is the length of the ray defining a contact point at $\theta$ degrees of flexion, a is a coefficient value between 20 and 50, and b is a coefficient value in a range of 0.00<b<0.30, wherein (i) c is a coefficient value between −0.010 and 0.00 and (ii) d is a coefficient value between −0.00015 and 0.00.

15. A posterior stabilized orthopaedic knee prosthesis comprising:

a femoral component including (i) a first condyle spaced apart from a second condyle to define an intracondylar notch therebetween, the first condyle including a first condyle surface and the second condyle including a second condyle surface, and (ii) a posterior cam positioned in the intracondylar notch; and a tibial bearing including (i) a platform having a bearing surface configured to articulate with the first condyle surface of the femoral component and (ii) a spine extending upwardly from the platform, wherein the first condyle surface of the femoral component (i) contacts the bearing surface at a first contact point on the first condyle surface at a first degree of flexion of about 0 degrees, (ii) contacts the bearing surface at a second contact point on the first condyle surface at a second degree of flexion, the second degree of flexion being greater than the first degree of flexion and in the range of about 30 degrees to about 50 degrees, and (iii) contacts the bearing surface at a third contact point on the first condyle surface at a third degree of flexion, the third degree of flexion being greater than the second degree of flexion and in the range of about 70 degrees to about 120 degrees, wherein the condyle surface in the sagittal plane has a first radius of curvature at the first contact point, a second radius of curvature at the second contact point, and a third radius of curvature at the third contact point, the first radius of curvature being different from the second radius of curvature and the third radius of curvature, wherein the posterior cam of the femoral component includes an anterior surface that is configured to initially contact the spine of the tibial bearing at a fourth degree of flexion, the fourth degree of flexion being at least 70 degrees, wherein the first condyle surface and the second condyle surface are curved and asymmetrical in the sagittal plane, and wherein the first condyle surface has a plurality of radii of curvature between the first contact point and the second contact point to transition from the first radius of curvature to the second radius of curvature over a range of degrees of flexion, each of the plurality of radii of curvature originating from a common origin and having a radius of curvature that is different than the radius of curvature of every other of the plurality of radii of curvature.

16. The posterior stabilized orthopaedic knee prosthesis of claim 15, wherein the condyle surface contacts the bearing surface at a plurality of contact points between the first contact point and the second contact point when the femoral component is moved from the first degree of flexion to the second degree of flexion, and each contact point of the plurality of contact points is defined by a ray extending from a common origin to the respective contact point of the plurality of contact points, each ray having a length defined by the following polynomial equation:

$$r_\theta = (a + (b*\theta) + (c*\theta^2) + (d*\theta^3)),$$

wherein $r_\theta$ is the length of the ray defining a contact point at $\theta$ degrees of flexion, a is a coefficient value between 20 and 50, and b is a coefficient value in a range of 0.00<b<0.30, wherein (i) c is a coefficient value between −0.010 and 0.00 and (ii) d is a coefficient value between −0.00015 and 0.00.

* * * * *